US012667304B2

(12) United States Patent
Kay et al.

(10) Patent No.: US 12,667,304 B2
(45) Date of Patent: Jun. 30, 2026

(54) MULTI-FUNCTION DEVICE FOR IMPROVING SLEEP AND METHOD OF OPERATION THEREOF

(71) Applicant: Hatch Baby, Inc., Palo Alto, CA (US)

(72) Inventors: Martin John Kay, Napa, CA (US); Amanda Yim Amyx, Chicago, IL (US); Adam Reineck, Mill Valley, CA (US); Stuart Gregory Tyrrell, Bainbridge Island, WA (US); Jillian Locks, Mill Valley, CA (US); Catherine Coffman Hammill, Redwood City, CA (US); Ann Crady Weiss, Palo Alto, CA (US); David Weiss, Palo Alto, CA (US)

(73) Assignee: HATCH BABY, INC., Palo Alto, CA (US)

( * ) Notice: Subject to any disclaimer, the term of this patent is extended or adjusted under 35 U.S.C. 154(b) by 23 days.

(21) Appl. No.: 18/977,303

(22) Filed: Dec. 11, 2024

(65) Prior Publication Data

US 2025/0099030 A1 Mar. 27, 2025

Related U.S. Application Data

(62) Division of application No. 18/324,059, filed on May 25, 2023, now Pat. No. 12,193,833.

(51) Int. Cl.
*A61B 5/00* (2006.01)

(52) U.S. Cl.
CPC .... *A61B 5/4815* (2013.01); *A61B 2560/0204* (2013.01); *A61B 2562/164* (2013.01)

(58) Field of Classification Search
CPC .......... A61B 5/4815; A61B 2560/0204; A61B 2562/164
See application file for complete search history.

(56) References Cited

U.S. PATENT DOCUMENTS

| | | |
|---|---|---|
| 2014/0170920 A1 | 6/2014 | Manipatruni et al. |
| 2019/0104993 A1* | 4/2019 | Reuveny .............. A61B 5/4818 |
| 2020/0091746 A1 | 3/2020 | Chien |
| 2023/0041557 A1 | 2/2023 | Lee et al. |
| 2023/0091548 A1 | 3/2023 | Weiss et al. |
| 2023/0092392 A1* | 3/2023 | Axelrod .............. F21V 33/0056 362/355 |
| 2024/0389935 A1 | 11/2024 | Kay et al. |

FOREIGN PATENT DOCUMENTS

WO WO 2024/242746 11/2024

* cited by examiner

*Primary Examiner* — Omeed Alizada
(74) *Attorney, Agent, or Firm* — Brooks Kushman, P.C.

(57) ABSTRACT

A multifunction device for improving sleep and methods of use are disclosed herein. The device can comprise an outer housing, a front panel, a front textile wrapped partially around the front panel, a plurality of LEDs within the outer housing, and an internal reflector coupled to the outer housing. The internal reflector can be configured to reflect light generated by the plurality of LEDs towards the front textile such that the light generated by the plurality of LEDs shines through the front panel and the front textile when a sleep-related program of the multifunction device is automatically initiated.

8 Claims, 14 Drawing Sheets

MULTI-FUNCTION DEVICE FOR IMPROVING SLEEP AND METHOD OF OPERATION THEREOF

CROSS-REFERENCE TO RELATED APPLICATIONS

This application is a divisional of U.S. patent application Ser. No. 18/324,059 filed May 25, 2023, which is incorporated herein by reference in its entirety.

FIELD OF TECHNOLOGY

The present disclosure relates generally to the field of sleep improvement devices, and, more specifically, to a multi-function sleep training device with sunrise and sunset clock features.

BACKGROUND

One way to encourage healthy sleeping habits is by establishing a regular bedtime routine using visual and auditory cues generated by sleep training devices such as nightlights or white-noise machines, respectively. However, traditional nightlights, alarm clocks, and white-noise machines often must be controlled by manually-operated switches or buttons which require the user to fumble with such controls in a dimly lit room. In addition, users often must program and set each device individually, which elongates a nighttime routine. Furthermore, such devices often take up valuable shelf space or table space on a nightstand or dresser.

Also, a sleep deprived or distracted user may forget to activate or set one or more sleep training devices, which may necessitate a user having to return to a room where someone is sleeping. In addition, some nightlights can be visually bright without proper dimming or audially inconsistent without proper sound control, which can disrupt a user's sleep.

Therefore, a solution is needed that can assist users with establishing healthy and regular sleeping routines by combining the beneficial features of multiple sleep training devices. In addition, such a solution should allow a user to control the device remotely and schedule programs which automatically activate certain visual and auditory cues. Moreover, such a solution should allow for the lights to be controlled by a dimming feature to lessen light disturbance during the night and a sound sealing feature to control sound disturbance during the night. Furthermore, the solution should not be overly complex and should be cost-effective to manufacture.

SUMMARY

In some aspects, disclosed a sleep training device, comprising: an outer housing; a front panel at a front side of the outer housing, a front textile wrapped partially around the front panel, wherein the front textile comprising a woven fabric comprising warp threads running vertically and weft threads running horizontally, wherein the warp threads are undyed, wherein the weft threads are dyed; a printed circuit board (PCB) comprising one or more processors and one or more memory units configured to store a sleep-related program; a plurality of LEDs within the outer housing and electrically coupled to the one or more processors; and an internal reflector, wherein the front panel is coupled to an edge of the internal reflector, wherein the internal reflector is configured to reflect light generated by the plurality of LEDs towards the front textile such that light generated by the plurality of LEDs shines through the front panel and the front textile when the sleep-related program is initiated.

In some aspects, the device further comprises a main speaker partially within a main speaker housing, wherein the main speaker housing is coupled to the internal reflector and is positioned rearward of the internal reflector, and wherein the main speaker faces a rear side of the outer housing.

In some aspects, the device further comprises a light dimming film positioned in front of a plurality of clock LEDs, and wherein the light dimming film is configured to dim light emitted by the plurality of clock LEDs.

In some aspects, the device further comprises a screen-printed layer covering a front face and edges of the front panel, and wherein the screen-printed layer is set via ultra-violet light.

In some aspects, the device further comprises a main LED dimmer positioned vertically over the plurality of LEDs, and wherein the plurality of LEDs face vertically upward.

In some aspects, the device further comprises a rear cover and a rear textile wrapped partially around the rear cover, wherein the rear textile comprises a woven fabric comprising warp threads running vertically and weft threads running horizontally, wherein the warp threads are undyed, and wherein the weft threads are dyed.

In some aspects, the device further comprises a capacitive touch component electrically coupled to the processor, and wherein the capacitive touch component is configured to be activated via touch through the front textile.

In some aspects, the outer housing is substantially shaped as a partial spherical segment.

In some aspects, the device further comprises a first button and a second button each positioned along a curved top of the outer housing, wherein a top surface of the first button is concave with respect to an exterior surface of the outer housing surrounding the first button, wherein a top surface of the second button is convex with respect to the exterior surface outer housing surrounding the second button, wherein the sleep-related program further comprises at least one of a wind-down program and a wake-up program, wherein the first button is configured to initiate the wind-down program, and wherein the second button is configured to initiate the wake-up program.

In some aspects, disclosed is a sleep training device, comprising: an outer housing and a housing base, wherein the outer housing comprises a front side, a rear side, and a curved top; a front panel at the front side of the outer housing; a rear cover at the rear side of the outer housing; a main speaker configured to produce sound, wherein the main speaker faces the rear side of the outer housing; an internal reflector, wherein the front panel is coupled to an edge of the internal reflector; and a main speaker housing coupled to the outer housing, wherein the main speaker is coupled to the main speaker housing, wherein the main speaker housing is substantially shaped as a partial spherical segment, wherein the main speaker housing, the internal reflector, and the main speaker create a sealed sound environment to control the sound produced by the main speaker.

In some aspects, the device further comprises a front textile wrapped partially around the front panel, wherein the front textile comprises a woven fabric comprising warp threads running vertically and weft threads running horizontally, wherein the warp threads are undyed, wherein the weft threads are dyed.

In some aspects, the main speaker housing is coupled to the internal reflector and is positioned rearward of the internal reflector, and wherein the main speaker faces a rear side of the outer housing.

In some aspects, the device further comprises a light dimming film positioned in front of a plurality of clock LEDs, and wherein the light dimming film is configured to dim light emitted by the plurality of clock LEDs.

In some aspects, the device further comprises a screen-printed layer covering a front face and edges of the front panel, and wherein the screen-printed layer is set via ultraviolet light.

In some aspects, the device further comprises a main LED dimmer positioned vertically over the plurality of LEDs, and wherein the plurality of LEDs face vertically upward.

In some aspects, the device further comprises a rear cover and a rear textile wrapped partially around the rear cover, wherein the rear textile comprises a woven fabric comprising warp threads running vertically and weft threads running horizontally, wherein the warp threads are undyed, and wherein the weft threads are dyed.

In some aspects, the device further comprises a capacitive touch component electrically coupled to the processor, and wherein the capacitive touch component is configured to be activated via touch through the front textile.

In some aspects, the outer housing is substantially shaped as a partial spherical segment.

In some aspects, disclosed is a sleep training device, comprising: an outer housing; a front panel at a front side of the outer housing, one or more printed circuit boards (PCBs) comprising one or more processors and one or more memory units mounted thereon, wherein the one or more memory units are configured to store a sleep-related program; a plurality of LEDs housed within the outer housing, wherein the plurality of LEDs face vertically upward; an internal reflector, wherein the front panel is coupled to an edge of the internal reflector, wherein the internal reflector is substantially shaped as a compound curve, wherein the internal reflector is configured to reflect light generated by the plurality of LEDs towards the front panel such that light generated by the plurality of LEDs shines through the front panel when the sleep-related program is initiated; and a main LED dimmer coupled to the internal reflector and positioned over the plurality of LEDs, wherein the main LED dimmer is configured to soften light generated by the plurality of LEDs before the light reaches the internal reflector.

In some aspects, the device further comprises a front textile wrapped partially around the front panel, wherein the front textile comprises a woven fabric comprising warp threads running vertically and weft threads running horizontally, wherein the warp threads are undyed, wherein the weft threads are dyed.

In some aspects, the device further comprises a main speaker partially within a main speaker housing, wherein the main speaker housing is coupled to the internal reflector and is positioned rearward of the internal reflector, and wherein the main speaker faces a rear side of the outer housing.

In some aspects, the device further comprises a light dimming film positioned in front of a plurality of clock LEDs, and wherein the light dimming film is configured to dim light emitted by the plurality of clock LEDs.

In some aspects, the device further comprises a screen-printed layer covering a front face and edges of the front panel, and wherein the screen-printed layer is set via ultraviolet light.

In some aspects, the device further comprises a rear cover and a rear textile wrapped partially around the rear cover, wherein the rear textile comprises a woven fabric comprising warp threads running vertically and weft threads running horizontally, wherein the warp threads are undyed, and wherein the weft threads are dyed.

In some aspects, the device further comprises a capacitive touch component electrically coupled to the processor, and wherein the capacitive touch component is configured to be activated via touch through the front textile.

In some aspects, the outer housing is substantially shaped as a partial spherical segment.

In some aspects, the main LED dimmer rests on a shelf of the internal reflector.

DETAILED DESCRIPTION

Figure 1:
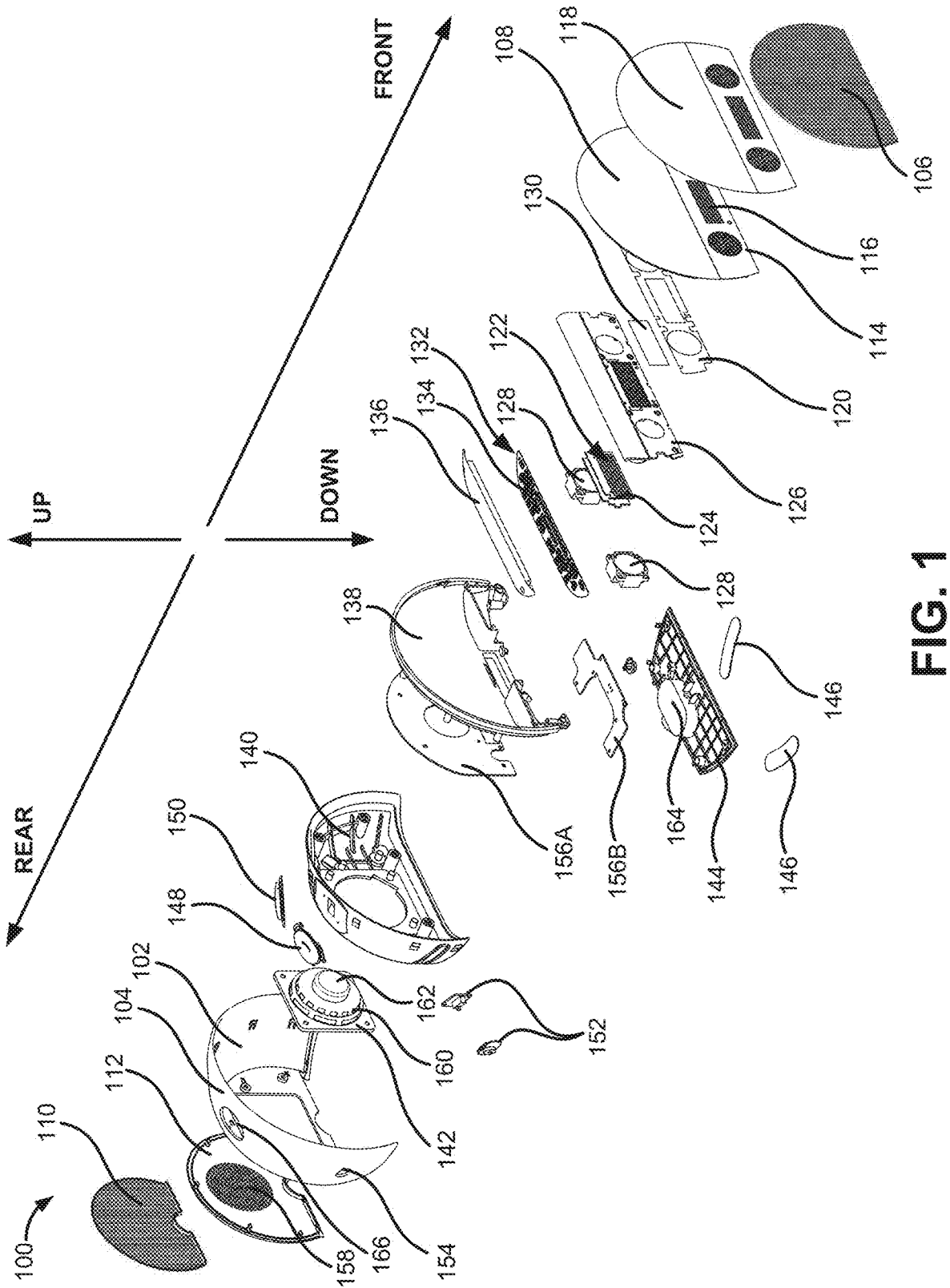
FIG. 1 illustrates an exploded view of an example of a sleep training device.

FIG. 1 illustrates an exploded view of a sleep training device 100. The sleep training device 100 can function as a combination sunrise alarm, nightlight, wind-down clock, alarm clock, and sound-emitting device. For example, the sleep training device 100 can produce light and sound(s) in a manner that aids a user in falling asleep as part of a wind-down routine and/or aids the user in waking up gently as part of a wake-up routine. The device 100 can generate sounds at varying volumes and emit light of varying colors and brightness during, before, and after both the wake-up routine and the wind-down routine.

The device 100 can comprise an outer housing 102, a front panel 108 coupled to a front side 200 of the outer housing 102, and a rear cover 112 coupled to a rear side 210 of the outer housing 102. The device 100 can also comprise a front textile 106 partially covering or otherwise coupled to the front panel 108 and a rear textile 110 partially covering or otherwise coupled to the rear cover 112.

The outer housing 102 can be shaped substantially as a partial spherical segment, a truncated bowl, or a partial frustoconical body. The device 100 can also comprise a substantially flat housing bottom 144 coupled to a base of the outer housing 102. The outer housing 102 can also be shaped substantially as a partial conic, a partial cylinder, a partial dome, or a combination thereof.

The flat housing bottom 144 can allow the device 100 to be placed on a substantially flat surface such as a tabletop, countertop, shelf, or nightstand top. The housing bottom 144 can comprise or be covered by one or more feet 146 comprising a friction pad or friction inducing surface or surface feature to prevent the device 100 from sliding off a placement surface or being inadvertently moved by a user. The feet 146 can be made of or can comprise rubber, synthetic rubber, a polymer having a high friction coefficient, or a combination thereof. The feet 146 can be substantially flat and shaped as an elongate oval (e.g., peanut-shaped), a circle, a rectangle, a rhombus, or a combination thereof. As seen in FIG. 2B, feet 146 can slightly raise the outer housing 102 from a platform.

The outer housing 102 can comprise a curved top 104 with multiple openings 166 or apertures defined along the curved top 104. The openings 166 or apertures can allow a user of the device 100 to access (e.g., apply a user input to) physical buttons that can be actuated to control the functionality of the device 100.

The device 100 can comprise a rest button 148 and a rise button 150. The rest button 148 and the rise button 150 can nest in or otherwise protrude through the openings 166 or apertures defined along the curved top 104 of the outer housing 102.

The rest button 148 can be concave with respect to an exterior surface of the outer housing 102 surrounding the rest button 148. The rest button 148 can be physically pressed when a user is ready to initiate a sleep-related program (e.g., a wind-down program). The rise button 150 can be convex with respect to an exterior surface of the outer housing 102 surrounding the rise button 150. The rise button 150 can be physically pressed when the user is ready to initiate another sleep-related program (e.g., a wake-up program). As will be discussed in more detail in later sections, the user can set the sleep-related program to control the lights and sounds emitted from the device 100.

Alternatively, the rest button 148 can be convex and the rise button 150 can be concave.

Also, the user can control the sleep-related program from a client device 502 (see FIG. 5) such as a smartphone, a tablet, a laptop, a smartwatch, a personal entertainment device, or a combination thereof.

In some variations, the rest button 148 and/or the rise button 150 (or additional buttons of the device 100) can also comprise one or more capacitive touch components or sensors.

The device 100 can also comprise a toggle switch 152. The outer housing 102 can comprise a toggle opening 154 or aperture along a lateral side of the outer housing 102 to allow the toggle switch 152 to be accessed by a user of the device 100.

The toggle switch 152 can be used to disable and enable an alarm program stored in a memory unit of the device 100. The toggle switch 152 can comprise a circular button that can move back and forth in the toggle opening 154. Part of the toggle switch 152 can be colored to indicate to the user when the alarm is enabled or disabled.

Any one of the outer housing 102, the rear cover 112, and the housing bottom 144 can be made in part of or comprise a polymeric material. For example, any one of the outer housing 102, the rear cover 112, and the housing bottom 144 can be made in part of or comprise acrylonitrile butadiene styrene (ABS), polycarbonate (PC), polypropylene (PP), one or more acrylics, a combination or composite thereof, or any such combination with a polymeric material.

Any one of the outer housing 102, the rear cover 112, and the housing bottom 144 can be made in part of a metallic material, a thermoplastic, a ceramic, or a combination thereof. For example, any one of the outer housing 102, the rear cover 112, and the housing bottom 144 can be manufactured as one molded piece of ABS plastic. In some variations, a portion of the outer housing 102 can be made of an organic material such as wood or bamboo.

The device 100 can also comprise a battery 164. The battery 164 can be coupled to housing bottom 144. The battery 164 can be powered via a power supply port 214 on the battery, which is accessible through outer housing 102, as seen in FIG. 2C.

The outer housing 102 can also be used to house, contain, or store a portable power supply such as one or more portable batteries. The batteries can include rechargeable batteries, one-time use batteries, or a combination thereof. For example, the batteries can include multiple C size batteries or multiple AA size batteries. The batteries can be alkaline batteries, lithium-ion batteries, nickel cadmium batteries, or nickel metal hydride batteries. The batteries can be positioned within a space in the main speaker housing 140.

The front panel 108 can be fastened, adhered, or otherwise coupled to the front side 200 of the outer housing 102. The rear cover 112 can be fastened, adhered, or otherwise coupled to the rear side 210 of the outer housing 102.

As will be discussed in more detail in later sections, at least part of the rear cover 112 can be defined by holes or openings arranged in a clustered circular pattern that allow that part of the rear cover 112 to function as a rear speaker grill 158.

The front panel 108 can be made in part of or can comprise a polymeric material. For example, the front panel 108 can be made in part of poly(methyl methacrylate) (PMMA), acrylonitrile butadiene styrene (ABS), or polycarbonate (PC).

As will be discussed in more detail in later sections, at least parts of the front panel 108 can be defined by holes or openings arranged in clustered circular patterns that allow those parts of the front panel 108 to function as front speaker grills 300.

Figure 3A:
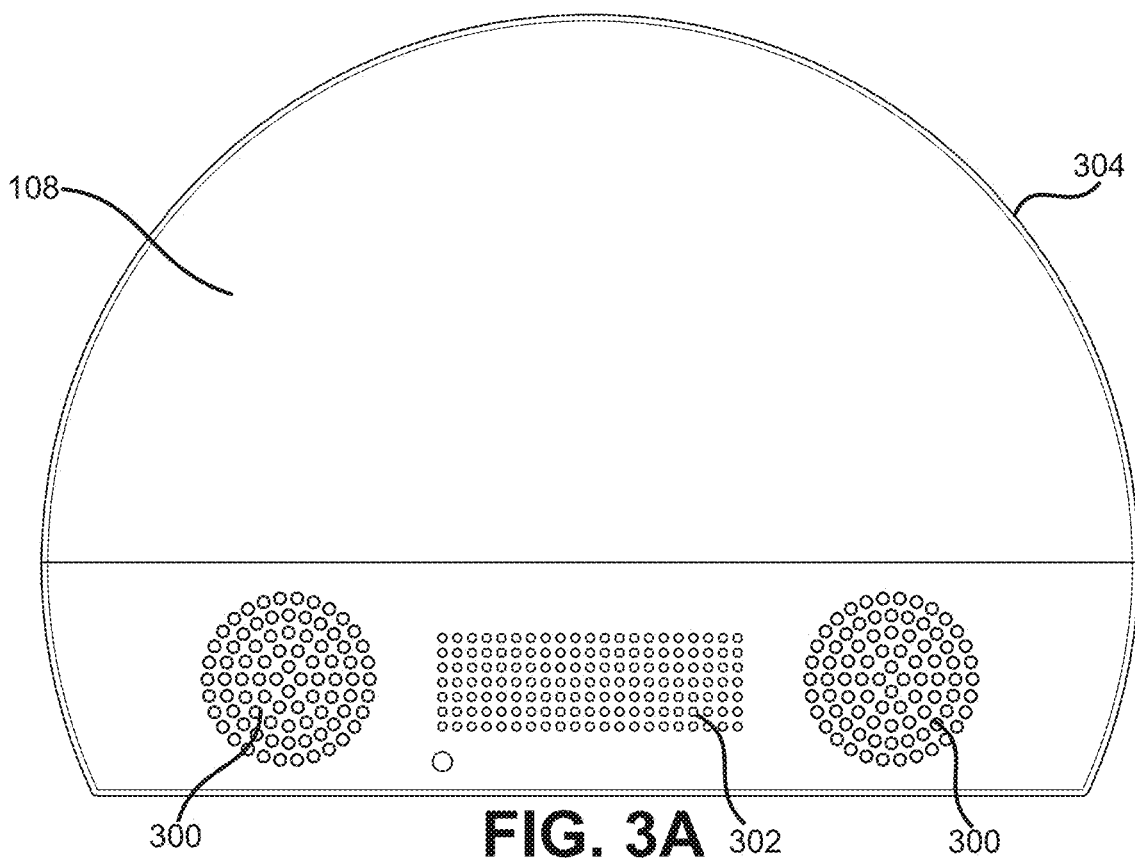
FIG. 3A illustrates a front view of a front panel of the sleep training device.

Moreover, as seen in FIG. 3A, at least part of the front panel 108 can be defined by holes or openings 302 arranged in a clustered rectangular pattern that allow that part of the front panel 108 to act as a clock display 204.

Referring back to the front textile 106 and the rear textile 110, the front textile 106 can be wrapped partially around the front panel 108 and the rear textile 110 can be wrapped partially around the rear cover 112. For example, the front textile 106 can be wrapped around an outer edge of the front panel 108. Also, for example, the rear textile 110 can be wrapped around an outer edge of the rear cover 112.

Each of the front textile 106 and the rear textile 110 can be a piece of woven fabric comprising warp threads running vertically and weft threads running horizontally, as seen with respect to the x-y axis in FIG. 2B. The warp threads can be undyed, and the weft threads can be dyed.

For example, each of the front textile 106 and the rear textile 110 can be a piece of natural linen where the warp threads of the linen are undyed and the weft threads of the linen are dyed.

Alternatively, the front textile 106 and the rear textile 110 can be made out of other materials such as synthetic fabrics, cotton, other fabrics, a combination thereof, or a combination of such materials and natural linen derived from flax.

The warp threads can be a set of threads running vertically and serving as the foundation of the textile. The weft threads can be a set of threads running horizontally. The weft threads can be woven to be substantially perpendicular to the warp threads, creating a crisscross pattern to the textile. The warp threads can be undyed, and the weft threads can be dyed. This pattern can allow the textile (e.g., the front textile 106) to create a dimming effect or dim the light that is emitted through the textile.

In some variations, the warp threads can be dyed and the weft threads can be undyed.

Each of the front textile 106 and the rear textile 110 can be covered by a polymeric coating. For example, each of the front textile 106 and the rear textile 110 can be covered by a dynamic silicone coating.

One technical problem faced by the applicant is how to design a sleep training device 100 (e.g., a combination sunrise alarm, nightlight, wind-down clock, alarm clock, and sound-emitting device) that is aesthetically-pleasing in a bedroom environment and that does not look like an obtrusive piece of high-tech equipment. One technical solution discovered and developed by the applicant is to cover a front and a rear of the sleep training device 100 with the specially-designed textiles as disclosed herein. The textiles add visual appeal to the sleep training device 100, making the device 100 look almost rustic and allows the device 100 to blend into a bedroom environment. Moreover, the specially-designed textiles as disclosed herein also function to dim and soften the light emitted from within the interior of the device 100.

In other variations, in lieu of the front textile 106 and/or the rear textile 110, the front and rear of the device 100 can be covered by polymeric components that allow light to shine through.

The front panel 108 can also have a screen-printed layer 118 coating or otherwise covering a front-facing surface and edges of the front panel 108. The screen-printed layer 118 can create a feathered or blurry gradient to diffuse light transmitted through the front panel 108. The screen-printed layer 118 can soften or dim light generated by lights (e.g., LEDs) within the interior of the device 100.

The screen-printed layer 118 can be printed or adhered onto the front-facing surface and the edges of the front panel 108. The screen-printed layer 118 can also provide the added functionality of protecting the edges of the front panel 108 from inadvertently damaging the front textile 106. The screen-printed layer 118 can be first applied to the front-facing surface and the edges of the front panel 108 and set via ultraviolet light.

The device 100 can also comprise a capacitive touch component 120. The capacitive touch component 120 can be located at the front side 200 of the outer housing 102 behind the front panel 108. The capacitive touch component 120 can match a shape or a design of a lower portion of the front panel 108. The capacitive touch component 120 can be electrically coupled to a processor of the device 100.

In other variations, the capacitive touch component 120 can be adhered to at least part of the front panel 108. In other variations, the capacitive touch component 120 can comprise at least part of the front panel 108.

The capacitive touch component 120 can also be located under the outer housing 102 at the curved top 104 of the device 100 for the purpose of displaying the time when the user taps the curved top 104 of the device 100.

The capacitive touch component 120 can be activated by a user touching part of the front textile 106. Upon activation of the capacitive touch component 120, a user can control a brightness and a volume of the device 100, as described further herein with respect to FIG. 2B.

A user can also physically contact or touch the capacitive touch component 120 through the front textile 106 and the front panel 108 to power on the device 100 or show the clock display 204 (as seen in FIG. 2B). In addition, a user can also cycle through one or more preset settings of light and/or sound by continuously touching or making physical contact with the capacitive touch component 120 through the front textile 106 and the front panel 108.

The capacitive touch component 120 can be made of or comprise a metallic material, a semiconductor material, or a combination thereof. For example, the capacitive touch component 120 can be made of or can comprise stainless steel.

The device 100 can also comprise a plurality of clock light-emitting diodes (LEDs) 122. The clock LEDs 122 can be positioned facing the front of the device 100, behind the front panel 108. The clock LEDs 122 can comprise a grid of 21×7 individual LEDs in a rectangular pattern. Alternatively, the clock LEDs 122 can comprise a grid of about 10-100 LEDs across about 5-50 LEDs.

The clock LEDs 122 can be configured to emit light through the front textile 106 and the front panel 108 to display time to the user via a clock display 204, as seen in FIG. 2B. The clock LEDs 122 can also display patterns such as a moon and stars or a sun to indicate to the user whether a wind-down routine or a wake-up routine is in progress.

The device can also comprise an internal lower front portion 126. The internal lower front portion 126 can comprise speaker receptacles 306 for insertion of one or more front speakers 128 (as seen in FIG. 3A). The internal lower front portion 126 can comprise clock LED openings 302 between the speaker receptacles 306 through which the clock LEDs 122 can be viewed by a user.

The internal lower front portion 126 can be placed in front of clock LEDs 122. The internal lower front portion 126 can be placed behind the capacitive touch component 120 and the front panel 108.

The internal lower front portion 126 can be made in part of or comprise a polymeric material, a metallic material, or a combination thereof. For example, the internal lower front portion 126 can be made in part of or comprise acrylonitrile butadiene styrene (ABS), polycarbonate (PC), polypropylene (PP), one or more acrylics including opal acrylic, or any such combination with a metallic material.

The device can also comprise a clock LED board 124. The clock LEDs 122 can be placed on, affixed, or otherwise coupled to the clock LED board 124. The clock LED board 124 can be shaped and sized to accommodate the clock LEDs 122. The clock LED board 124 can be coupled to the internal lower front portion 126.

The device 100 can also comprise a light dimming film 130. The light dimming film 130 can be placed over the clock LED openings 302 of internal lower front portion 126. The light dimming film 130 can soften the light emitted from the clock LEDs 122. For example, the light dimming film 130 can be tinted with a substantially yellow color. The light dimming film 130 can be made of semi-translucent plastic such as an acrylic (e.g., an opal acrylic).

Alternatively, the light dimming film 130 can be made of in part of or comprise another type of polymeric material. For example, the light dimming film 130 can be made in part of or comprise polypropylene (PP), acrylonitrile butadiene styrene (ABS), polycarbonate (PC), a combination thereof, or any such combination with an acrylic.

The device 100 can also comprise one or more main LEDs 132. The main LEDs 132 can be placed on a main LED board 134 positioned rearward of the internal lower front portion 126. The main LEDs 132, in aggregate, can be arranged in a trapezoidal pattern, a rectangular pattern, a rhombus-shaped pattern, a triangular pattern, a ring-like pattern, or an oval pattern on the main LED board 134.

Although only a one-level or single-layer arrangement of main LEDs 132 is shown in FIG. 1, it is contemplated by this disclosure that multiple layers or levels of main LEDs 132 can be stacked on top of one another. The main LEDs 132 can also be arranged such that each LED 132 is separated from its adjacent neighboring LED 132 by a space or gap. The main LEDs 132 can face vertically upward.

Both the main LEDs 132 and the clock LEDs 122 can include one or more red-green-blue-white (RGBW) LEDs. The main LEDs 132 and the clock LEDs 122 can also include one or more active-matrix organic light-emitting diodes (AMOLED), a super AMOLEDs, or a combination thereof.

The device 100 can also comprise a main LED dimmer 136. The main LED dimmer 136 can be positioned vertically over the main LED board 134. The main LEDs 132 can emit light that passes through the main LED dimmer 136. The main LED dimmer 136 can be configured to diffuse or soften light generated by the main LEDs 132 before light reaches the front side 200 of the device 100. Accordingly, the main LED dimmer 136 can be shaped to cover an entirety of the main LED board 134.

The main LED dimmer 136 can be made of clear plastic. The main LED dimmer 136 can also be made of or comprise a polymeric material configured to dissipate heat generated by the main LEDs 132. For example, the main LED dimmer 136 can be made of or comprise ABS, polycarbonate, a combination thereof, or any such combination with a polymeric material.

The main LED dimmer 136 can also comprise or can be defined by one or more surface features or textures configured to diffuse light generated by the main LEDs 132. The main LED dimmer 136 can also be covered by one or more coatings configured to diffuse light or dissipate heat generated by the main LEDs 132.

The device 100 can also comprise an internal reflector 138. The internal reflector 138 can be positioned behind or rearward of the front panel 108. The internal reflector 138 can comprise a compound curve shape that is concave towards the front side of the device 100. The compound curve shape of the internal reflector 138 can direct light generated by the main LEDs 132 to the front side of the device 100. As such, light generated by the main LEDs 132 can shine through the front panel 108 and the front textile 106 when a sleep-related program is initiated.

The front panel 108 can be coupled to an edge of the internal reflector 138 such that the front panel 108 nests partially within the internal reflector 138. As will be further described with respect to FIGS. 4A and 4B, the internal reflector can comprise features such as shelves to accommodate the main LED dimmer 136 and the main LED board 134.

One technical problem faced by the applicants is how to design the device 100 such that the light emitted from the main LEDs 132 is dimmed for the user so as to not disturb their sleep. One technical solution discovered and developed by the applicants is the set up disclosed herein where the main LED dimmer 136 diffuses light before the internal reflector 138 directs light generated by the main LEDs 132 toward the front textile 106. The front textile 106 can also be manufactured to diffuse or dim the light in order to dim or control the light experienced by the user.

The device 100 can also comprise a main speaker housing 140 and a main speaker 142. The main speaker housing 140 can be configured to couple to part of the main speaker 142. The main speaker housing 140 can be sized to fit within outer housing 102. The main speaker housing 140 along with the internal reflector 138 and the main speaker 142 can create a sealed sound environment to control the sound produced by the main speaker 142.

The main speaker housing 140 can be substantially shaped as a partial spherical segment, a truncated bowl, or a partial frustoconical body.

In one variation, the main speaker housing 140 can be detachable or separable from the outer housing 102. In other variations, the main speaker housing 140 can be affixed to the outer housing 102 by adhesives, fasteners, a threaded connection, or a combination thereof.

The main speaker housing 140 can be made in part of or comprise a polymeric material, a metallic material, or a combination thereof. For example, the main speaker housing 140 can be made in part of or comprise acrylonitrile butadiene styrene (ABS), polycarbonate (PC), polypropylene (PP), one or more acrylics, a combination or composite thereof, or any such combination with a metallic material.

The main speaker 142 can be controlled by one or more electronic components of the device 100. In addition to supporting the main speaker 142, the main speaker housing 140 and/or the outer housing 102 can also house or function as a container for one or more electrical components such as wires, circuits, conductors, interfaces, circuit boards, power supply components, or a combination thereof. The electrical components can connect a processor or another circuit or chip on the PCB 156A to the main speaker 142, the capacitive touch component 120, or a combination thereof.

The main speaker 142 can have a cone 160 that faces rearward and a pole piece 162 that faces forward. The main speaker 142 can be positioned rearward of the internal reflector 138 and can face the rear side 210 of the outer housing 102. The main speaker 142 can emit sound toward the rear side 210 of the outer housing and through rear speaker grill 158 of rear cover 112 and the rear textile 110. The rear cover 112 (including the rear speaker grill 158) and the rear textile 110 can muffle or soften the sound emitted by the main speaker 142.

One technical problem faced by the applicants is how to configure the device 100 to control the sound emitted so as not to disturb the user during sleep. One technical solution discovered and developed by the applicants is the configuration disclosed herein where the main speaker 142 faces the rear of the device 100 and the main speaker housing 140, the main speaker 142, and the internal reflector 138 create a sealed sound environment to control and enhance the sound produced by the main speaker 142. Moreover, the main speaker 142 faces the rear of the device 100 such that the sound is partially muffled or softened by the rear cover 112 and the rear textile 110 such that the sound emitted is jarring when heard by a sleeping or dozing user.

The device can also comprise one or more printed circuit boards (PCBs) 156A and 156B. The one or more PCBs 156A or PCBs 156B can each comprise one or more chips, modules, integrated circuits (ICs), sensors, interfaces, and high-speed buses, or a combination thereof. The one or more PCBs 156A or PCBs 156B can be housed within the outer housing 102.

The PCB 156A can function to control main speaker 142. PCB 156A can be located between the main speaker housing 140 and the internal reflector 138. The PCB 156A can be shaped as a semicircular arch to fit within main speaker housing 140. The PCB 156A can be adhered to or coupled to main speaker housing 140. Alternatively, or additionally, PCB 156A can be adhered to or coupled to main speaker 142.

The PCB 156A and main speaker 142 can be coupled to one another or to the interior of the outer housing 102 by fasteners, screws, thread connections, interference fit, clips, clasps, adhesives, heat staking, thermoplastic staking via laser welding or ultrasonic welding, or a combination thereof. For example, PCB 156A, the main speaker 142, main speaker housing 140, internal reflector 138, or a combination thereof can be coupled to polymeric studs, posts, ribs, bosses, or any combination thereof protruding from an interior surface of a part of the outer housing 102 through holes or slots on any of the boards via staking or an interference fit.

The PCB 156B can function to control the main LEDs 132 and the clock LEDs 122. The PCB 156B can be located between the internal reflector 138 and the housing bottom 144 and under the main LED board 134. The main LED board 134 can be elevated from the PCB 156B such that the LED board 134 and the main LEDs 132 are separated from the electrical components on the PCB 156B by a gap or distance. The PCB 156B can be shaped so as to rest on the housing bottom 144.

The PCB 156B and the housing bottom 144 can be coupled to one another or to the interior of the outer housing 102 by fasteners, screws, thread connections, interference fit, clips, clasps, adhesives, heat staking, thermoplastic staking via laser welding or ultrasonic welding, or a combination thereof. For example, the PCB 156B, the main LED board 134, the housing bottom 144, the internal reflector 138, or a combination thereof can be coupled to polymeric studs, posts, ribs, bosses, or any combination thereof protruding from an interior surface of a part of the outer housing 102 through holes or slots on any of the boards via staking or an interference fit.

Figure 2A:
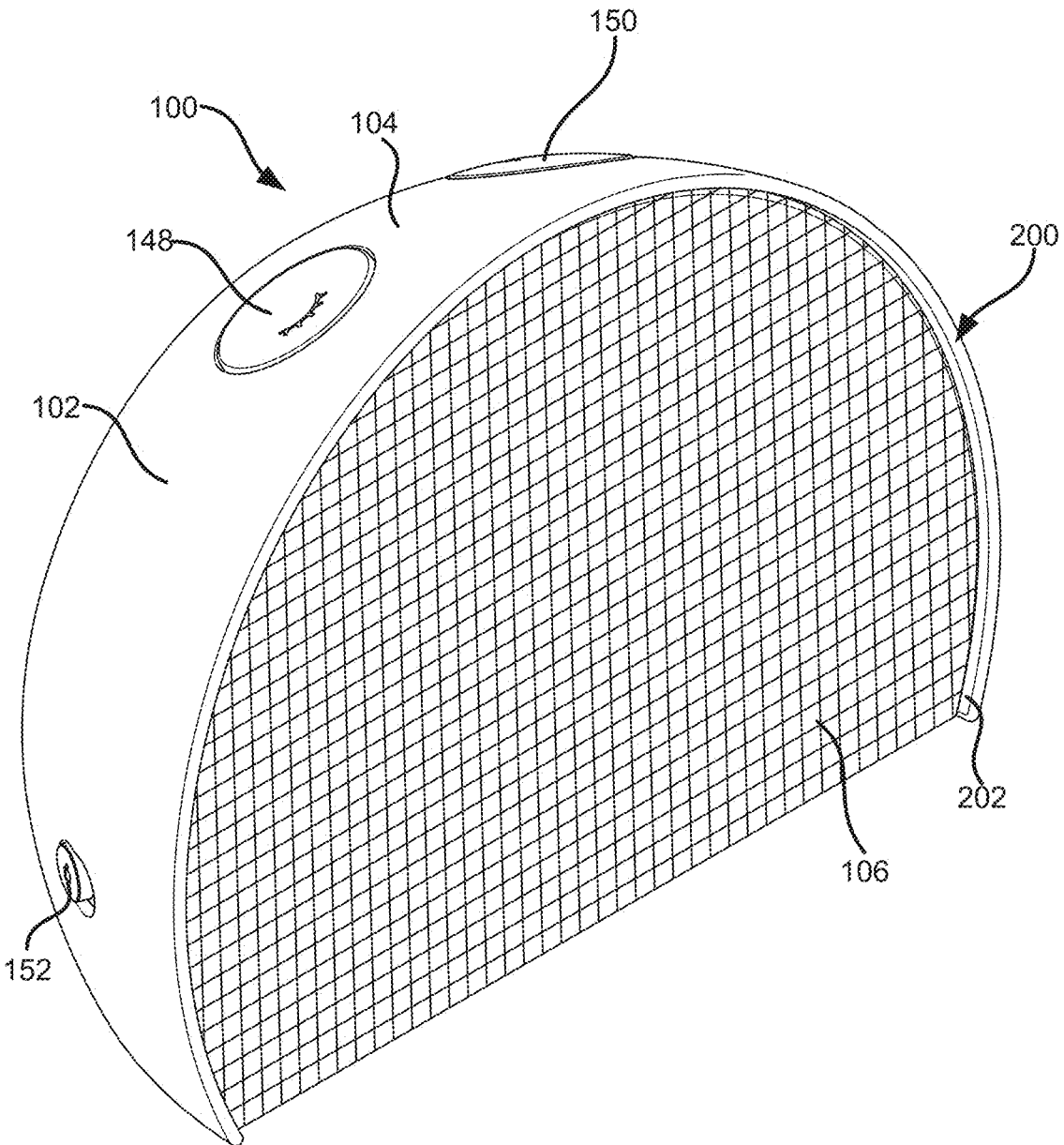
FIG. 2A illustrates a perspective view of an example of the sleep training device in an assembled configuration.
Figure 2B:
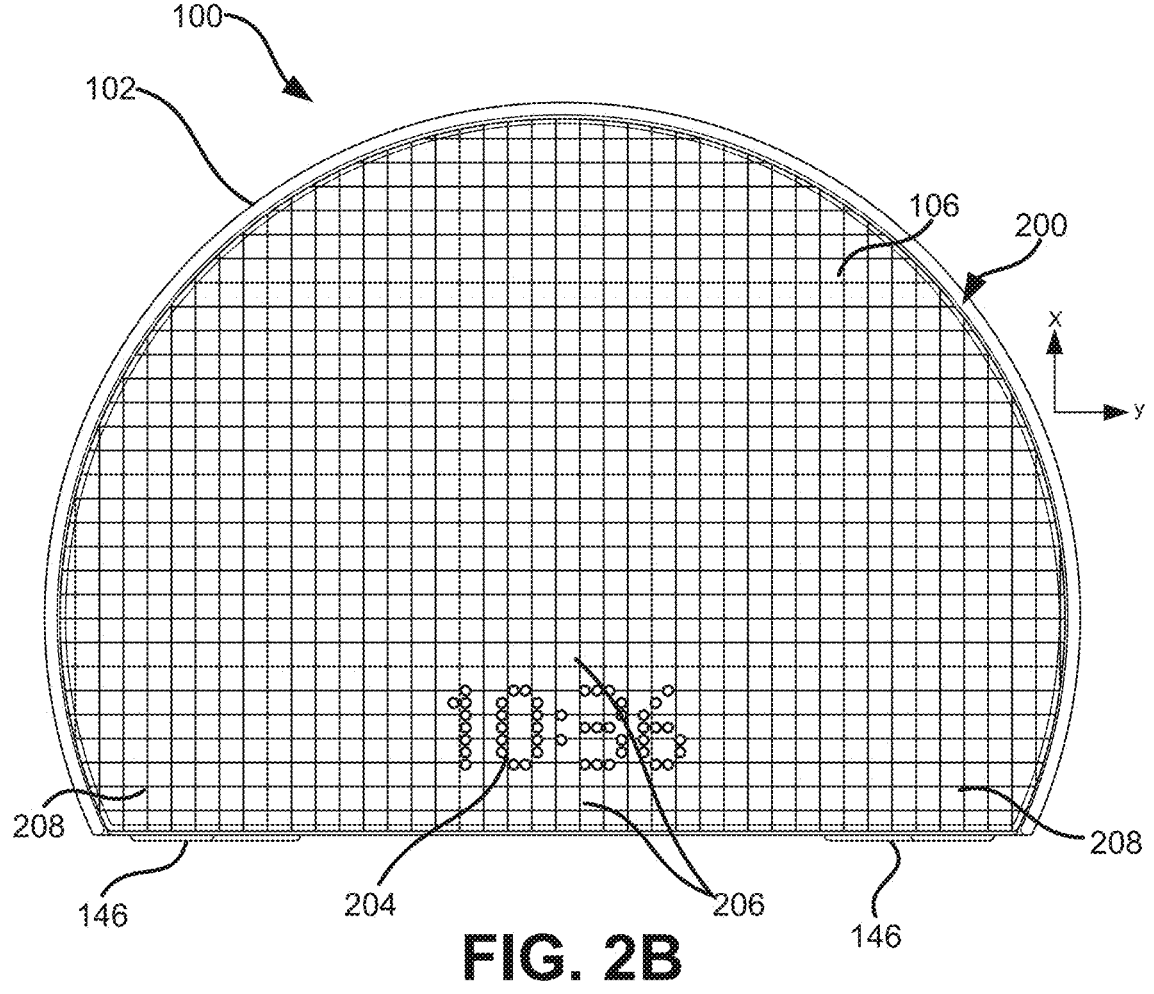
FIG. 2B illustrates a front view of the sleep training device.
Figure 2C:
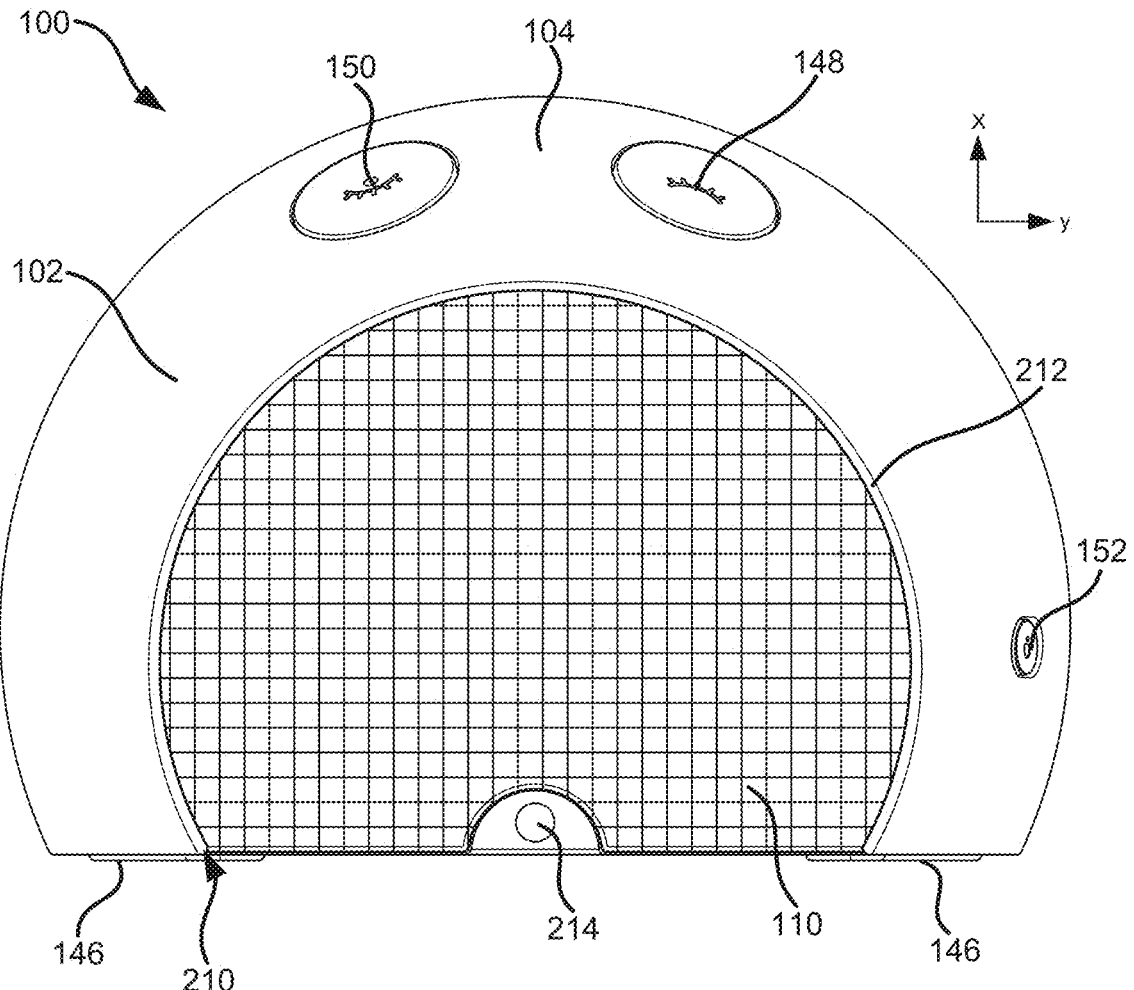
FIG. 2C illustrates a rear view of the sleep training device.

FIG. 2A illustrates a perspective view of an example of the sleep training device 100. The outer housing 102 can comprise a front side 200 comprising a front edge 202, as seen in FIG. 2A, and a rear side 210, as seen in FIG. 2C. The front side 200 of the outer housing 102 can be at least partially covered by the front textile 106. The front textile 106 can serve as a front face of the sleep training device 100.

The front textile 106 can be recessed from the front edge 202 or set slightly behind (or rearward of) the front edge 202 of the outer housing 102. The front edge 202 of the outer housing 102 can also partially shield the front textile 106 from damage during transport or otherwise regular use.

The rest button 148 can be concave with respect to an exterior surface of the curved top 104 of the outer housing 102 surrounding the rest button 148. The rest button 148 can be physically pressed when a user is ready to initiate a sleep-related program (e.g., a wind-down program).

The rise button 150 can be convex with respect to an exterior surface of the curved top 104 of the outer housing 102 surrounding the rise button 150. The rise button 150 can be physically pressed when the user is ready to initiate another sleep-related program (e.g., a wake-up program).

FIG. 2B illustrates a front view of the sleep training device 100. The device 100 can have a clock display 204 made up of a plurality of clock LEDs 122. The clock LEDs 122 can shine or emit light through the front textile 106 such that the clock display 204 is visible to the user through the front textile 106.

The clock display 204 can be positioned toward the bottom of the front side 200 of the outer housing 102. The clock display 204 can be connected to a real-time clock integrated circuit (IC) of the device 100.

Alternatively, the clock display 204 can also display symbols such as a moon and stars or a sun to indicate to the user whether a wind-down routine or a wake-up routine is in progress.

The device 100 can also comprise touch-enabled brightness control switches 206 and touch-enabled volume control switches 208. The brightness control switches 206 and the volume control switches 208 can be activated via the capacitive touch component 120 behind the front textile 106 and the front panel 108.

The brightness control switches 206 can be located above and below the clock display 204 on the front side 200 of the device 100. To increase the brightness of the device 100 during use, the user can physically contact or touch above the clock display 204. To decrease the brightness of the device 100 during use, the user can physically contact or touch below the clock display 204.

The volume control switches 208 can be located at lateral sides of the clock display 204 on the front side 200 of the device 100. To increase the volume of the device 100 during use, the user can physically contact or touch one side of the clock display 204 (i.e., to the right of the clock display 204 in FIG. 2B). To decrease the volume of the device 100 during use, the user can physically contact or touch another side of the clock display 204 (i.e., to the left of the clock display 204 in FIG. 2B).

FIG. 2C illustrates a rear view of the sleep training device 100. The rear side 210 of the outer housing 102 can be at least partially covered by the rear textile 110. The rear side 210 of the outer housing 102 can comprise a rear edge 212.

The rear textile 110 can be recessed from the rear edge 212 or set slightly behind (or forward of) the rear edge 212 of the outer housing 102. The rear edge 212 of the outer housing 102 can also partially shield the rear textile 110 from damage during transport or otherwise regular use.

The device 100 can also comprise a power supply port 214 for receiving a charging cable. The charging cable can be plugged into the power supply port 214 to charge the battery 164. The power supply port 214 can be accessed through openings or cutouts defined along the outer housing 102, the rear textile 110, and the rear cover 112. The power supply port 214 can include a universal serial bus (USB) port such as a micro-USB, a mini-USB port, or a USB-C port. The power supply port 214 can also be a coaxial barrel receptacle for receiving a coaxial barrel connector. For example, the power supply port 214 can receive a connector of a universal alternating current (AC) adapter.

Alternatively, or in addition to the battery 164, the device 100 can have an inductive charge receiver housed within the outer housing 102 for receiving wireless power.

Figure 2D:
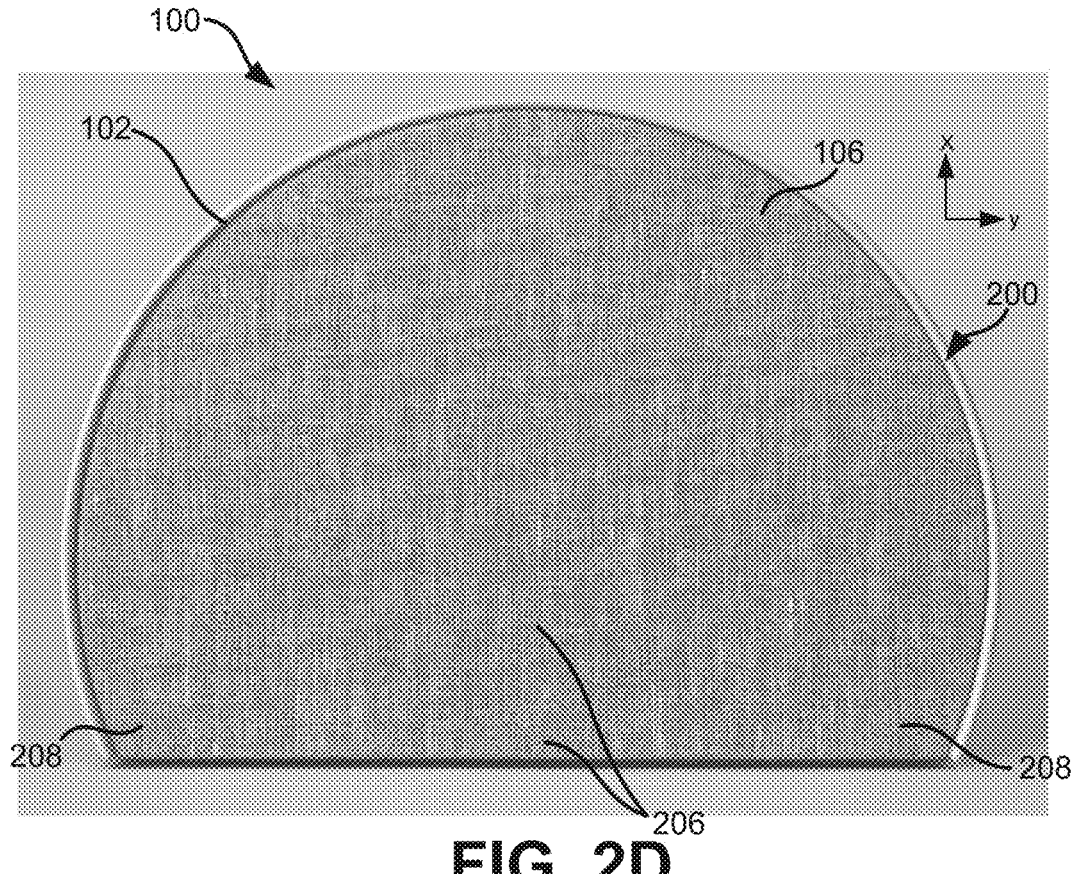
FIG. 2D is a black-and-white image showing a front view of an example of the sleep training device while not illuminated.

FIG. 2D illustrates another front view of the sleep training device 100. This view further shows the threads of the front textile 106 comprising warp threads running vertically and weft threads running horizontally. As shown in FIG. 2D, the warp threads can be undyed and the weft threads can be dyed. Threads can run horizontally and vertically with respect to the x-axis and the y-axis. The front textile 106 (along with the rear textile 110) adds visual appeal to the sleep training device 100. The front textile 106 (along with the rear textile 110) can also make the device 100 look almost rustic and allow the device 100 to blend into a bedroom environment. Moreover, the specially-designed front textile 106 can also function to dim and soften the light emitted by the main LEDs 132 from within the interior of the device 100.

Figure 2E:
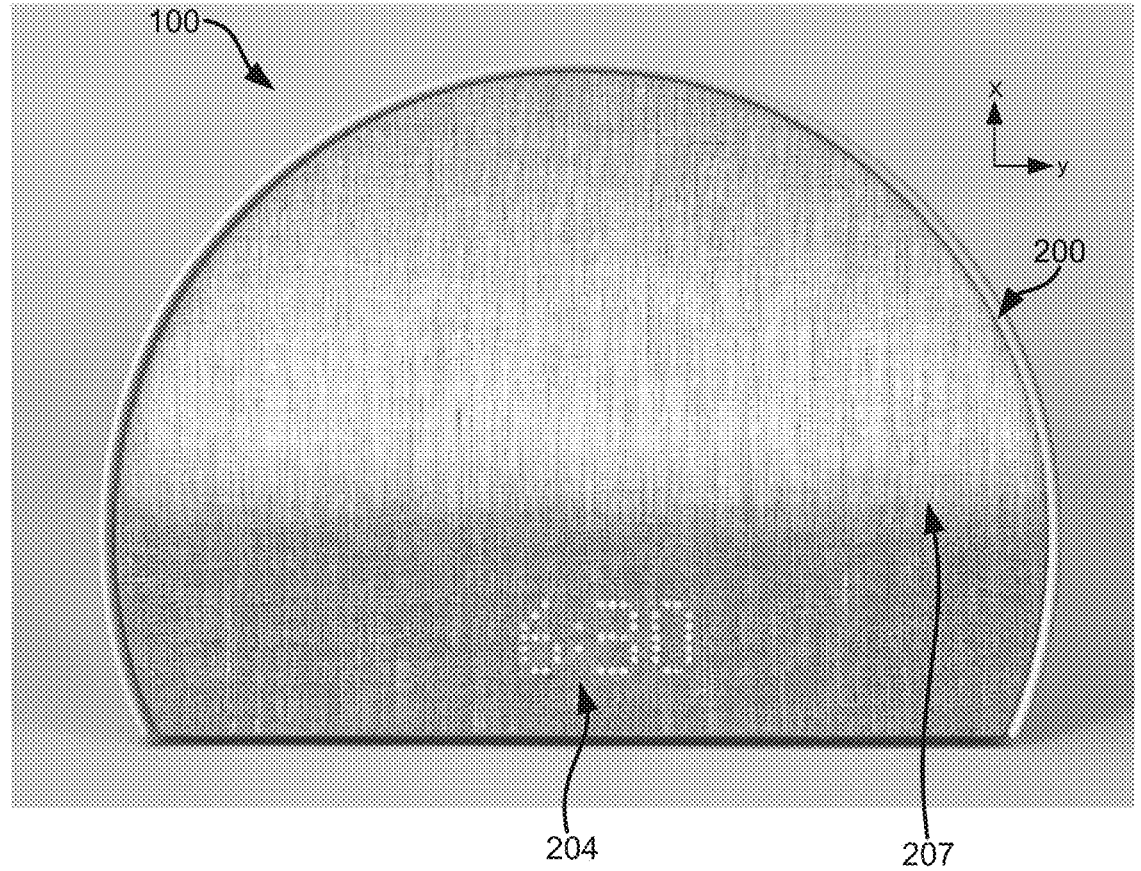
FIG. 2E is a black-and-white image showing a front view of an example of the sleep training device while illuminated.

FIG. 2E is a black-and-white image showing a front view of an example of the sleep training device 100 while illuminated. When the device 100 is illuminated via the main LEDs 132, the front textile 106 along with the front panel 108 and the screen-printed layer 118 can display a "sunrise" or "sunset" gradient along the front side 200 of the device 100. The screen-printed layer 118 can provide a feathered look to the device 100 when the device 100 is illuminated from within. This can reduce the harshness of the light and make the light emitted by the device 100 seem warmer. The screen-printed layer 118 can also create a transition region 207 along the front side 200 of the device 100 when the device 100 is illuminated from within. As shown in FIG. 2E, the transition region 207 can be a substantially horizontal region or horizontal band along the front side 200 of the device 100 where the light appears to dissolve or become blurry. In this manner, the device 100, when illuminated from within, appears to mimic the sun at sunset or sunrise.

One technical problem faced by the applicant is how to design the sleep training device 100 such that the device 100 displays a gentle light that imitates a sunrise or a sunset. One technical solution discovered and developed by the applicants is to provide a screen-printed layer 118 disposed over the front panel 108 to provide a blurred effect representing a sunrise or a sunset. The blurred effect is a gradual transition and can provide a gentle look to the front side 200 of the device 100. The blurred and feathery effects can be seen with any color emitted by the main LEDs 132.

FIG. 3A illustrates a front view of the front panel 108 of the sleep training device 100. The front panel 108 can comprise one or more front speaker grills 300 and one or more LED openings 302. Front speaker grills 300 can be positioned on either side of the LED openings 302. Each of the front speaker grills 300 can be comprised of multiple individual openings.

The front panel 108 can have a front panel edge 304 that can be configured to couple to the outer housing 102. The front textile 106 can also wrap around the front panel 108 such that at least a part of the front textile 106 nests between the front panel 108 and the outer housing 102.

The front panel 108 can comprise a plurality of LED openings 302 toward the bottom of the front panel 108. The plurality of LED openings 302 can be collectively arranged in a rectangular-shaped pattern.

The plurality of LED openings 302 can also be collectively arranged in a circular-shaped pattern, an oval-shaped pattern, a triangular-shaped pattern, a rhombus-shaped pattern, or a combination thereof.

Figure 3B:
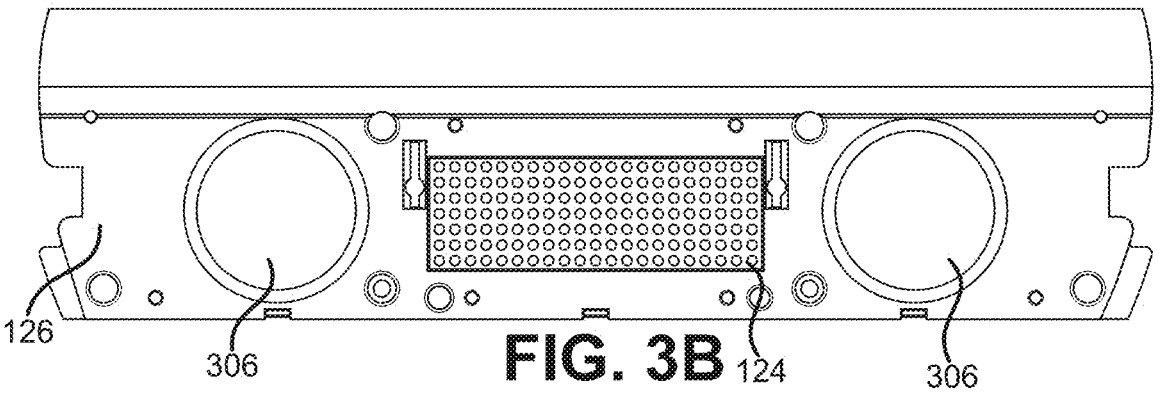
FIG. 3B illustrates a front view of an internal lower front portion of the sleep training device.

FIG. 3B illustrates a front view of the internal lower front portion 126 of the sleep training device. The internal lower front portion 126 can have one or more speaker receptacles 306. The one or more speaker receptacles 306 can serve as housing(s) for the front speakers 128.

The one or more speaker receptacles 306 can be positioned on either lateral side of the internal lower front portion 126.

Figure 3C:
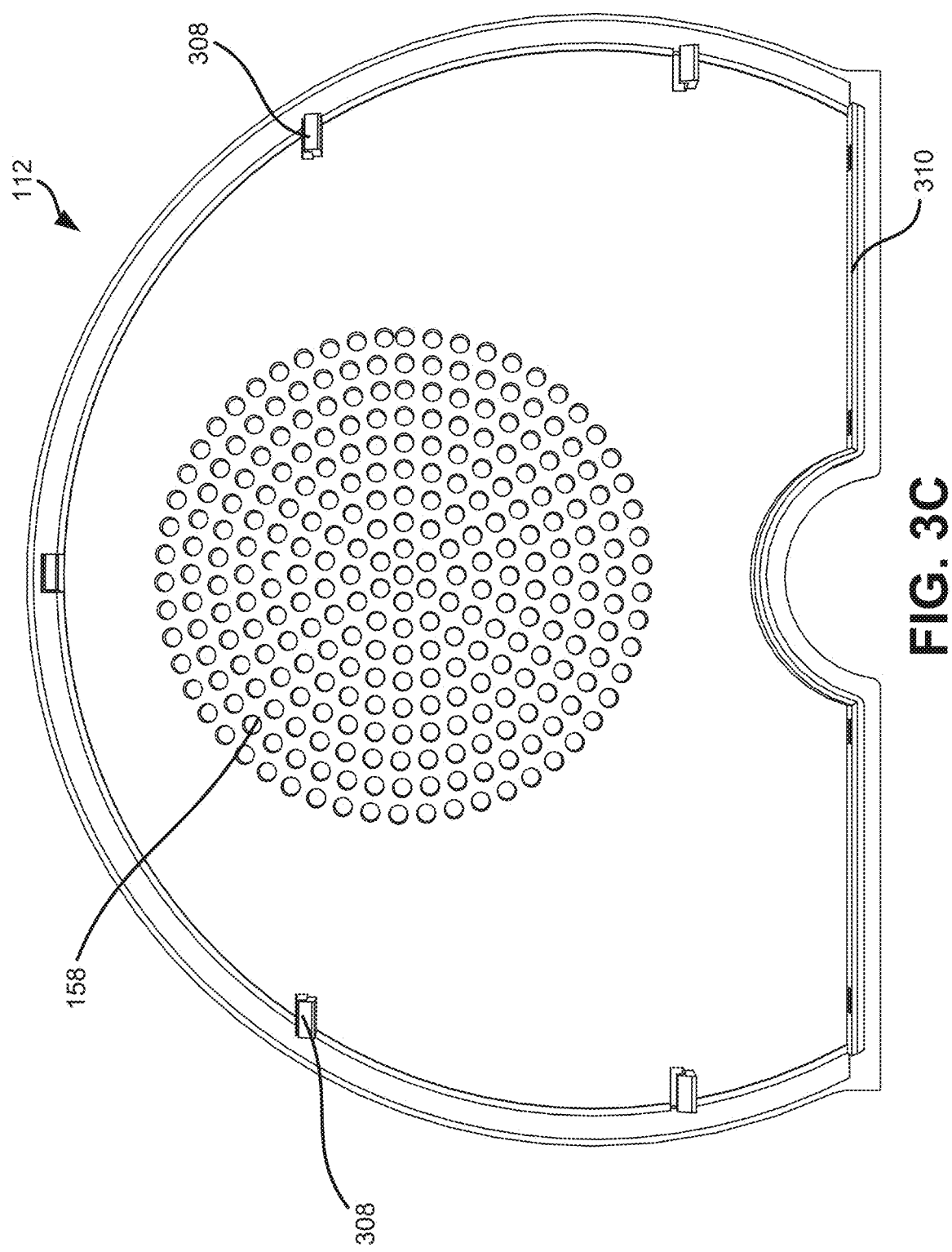
FIG. 3C illustrates a front view of a rear cover of the sleep training device.

FIG. 3C illustrates a front view of the rear cover 112 of the sleep training device 100. The rear cover 112 can comprise a rear speaker grill 158. The rear speaker grill 158 can be positioned substantially in a center of the rear cover 112. The rear speaker grill 158 can serve as a screen or cover for the main speaker 142. The rear speaker grill 158 can be comprised of a plurality of holes or openings arranged in clustered circular pattern.

Alternatively, the rear speaker grill 158 can be comprised of a plurality of holes or openings arranged in a substantially rectangular pattern, triangular pattern, or oval pattern.

The rear cover 112 can be made in part of or comprise a polymeric material. For example, the rear cover 112 can be made in part of poly(methyl methacrylate) (PMMA), acrylonitrile butadiene styrene (ABS), or polycarbonate (PC).

The rear cover 112 can also comprise snap fittings 308. The snap fittings 308 can be used to latch the rear cover 112 onto the outer housing 102. The snap fittings 308 can comprise a ledge to snap onto the rear side 210 of the outer housing 102.

The rear textile 110 can be wrapped at least partially around the rear cover 112. The rear textile 110 can wrap around the rear cover 112 such that at least a part of the rear textile 110 is disposed between the rear cover 112 and the outer housing 102.

The rear cover 112 can also comprise a rear cover edge 310. The rear cover edge 310 can be positioned towards a bottom of the rear cover 112. The rear cover edge 310 can be positioned slightly under and touching the outer housing 102 such that the rear cover 112 couples with the outer housing 102. The outer housing 102 can rest on the rear cover edge 310.

Figures 4A, 4B:
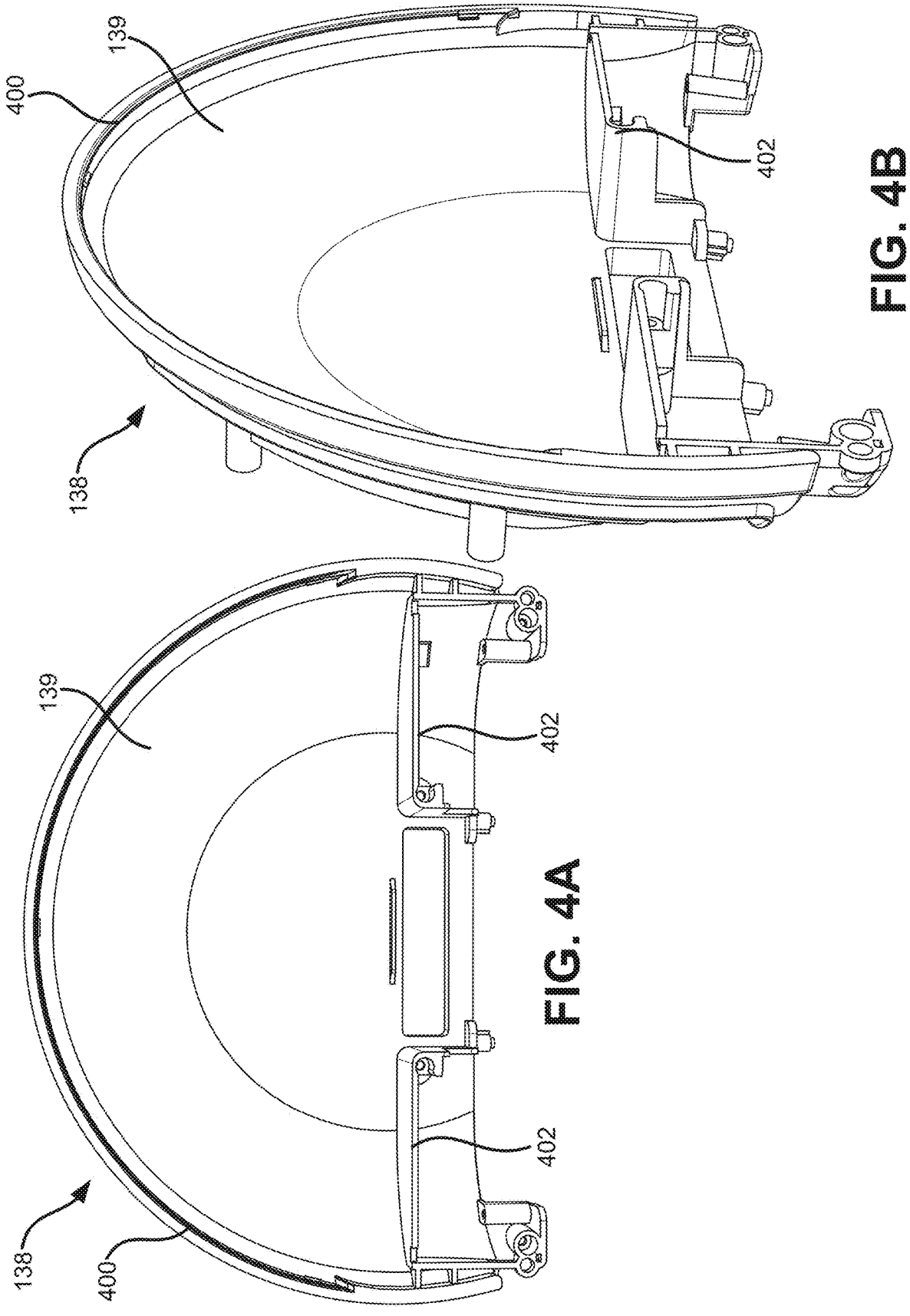
FIG. 4A illustrates a front view of an internal reflector of the sleep training device.
FIG. 4B illustrates a front perspective view of the internal reflector of the sleep training device.

FIG. 4A illustrates a front view of the internal reflector 138 of the sleep training device 100. The internal reflector 138 can comprise a ridge 400. The ridge 400 can extend at least partially along a front-facing side of the internal reflector 138. The front panel 108 of the device 100 (not shown in FIG. 4A) can snap into the ridge 400 in order to rest within the internal reflector 138 when assembled.

The internal reflector 138 can also comprise a shelf 402 on either side of the internal reflector 138. The shelf 402 can hold the main LED board 134 carrying the main LEDs 132 such that the main LEDs 132 face vertically upward. The main LED dimmer 136 can be positioned over the main LED board 134 and can be shaped to fit within the internal reflector 138 on top of the shelf 402.

The main LED dimmer 136 and the main LED board 134 can also be coupled to the internal reflector 138 via fasteners, screws, thread connections, or a combination thereof.

FIG. 4B illustrates a front perspective view of the internal reflector 138 of the sleep training device 100. The internal reflector 138 can comprise a curved back 139. The curved back 139 of the internal reflector 138 can be substantially shaped as a compound curve. The curved back 139 of the internal reflector 138 can be configured to reflect and direct light generated by the main LEDs 132 toward the front panel 108 such that light generated by the plurality of main LEDs 132 shines through the front panel 108 and the front textile 106 when a sleep-related program is initiated.

One technical problem faced by the applicant is how to design the sleep training device 100 such that light generated by the main LEDs 132 reach the user in way that softens and dims the light but still allows enough light to reach the user to wake up the user when a wake-up program is initiated. One technical solution discovered and developed by the applicant is to design the device 100 with the internal reflector 138 disclosed herein having a curved back 139 substantially shaped as a compound curve. The curved back 139 reflects and directs the light generated or emitted by the main LEDs 132 (positioned vertically upward) toward the front panel 108 and the front textile 110. In this manner, the light emitted by the device 100 that reaches the user appears warm and mimics sunlight shining through curtains of a window.

Referring back to FIG. 1, the device 100 can comprise one or more processors coupled to the PCB 156A and/or the PCB 156B. The one or more processors can comprise a communication unit processor, a system processor, or a combination thereof. The communication unit processor can be part of a communication chip along with a communication unit memory and a real time clock IC. The real time clock IC can be used by the processors to keep track of time when a user initiates a timer function through the application on the client device 502 (see FIG. 5) or sets a time-specific sleep-related program.

The communication chip can be part of a communication module coupled to the PCB 156A and/or 156B. The communication unit processor can also be coupled to an antenna.

For example, the communication module can be a Bluetooth® module and the communication chip can be a Bluetooth® communication chip and the antenna can be a Bluetooth® antenna. As a more specific example, the Bluetooth® communication chip can be a Nordic® nRF51822 Bluetooth® low energy (BLE) chip and the communication unit processor can be a 32-bit ARM® Cortex®-M0 processor.

In other instances, the communication module can be a WiFi module, the communication chip can be a WiFi chip, and the antenna can be a WiFi antenna. The device 100 can have both a Bluetooth® module or chip and a WiFi module or chip. References to a processor or processors in this disclosure can include references to the communication unit processor, the system processor, or a combination thereof.

The system processor can refer to one or more CPUs, GPUs, ASICs, FPGAs, or a combination thereof. The system processor can execute software stored in one or more memory units of the device 100 to execute the methods described herein.

The system processor can be implemented in a number of different manners, for example, the system processor can be an embedded processor, a processor core, a microprocessor, a logic circuit, a hardware FSM, a DSP, or a combination thereof. As a more specific example, the system processor can be a 32-bit processor such as an ARM™ processor.

The one or more memory units can store software, data, logs, or a combination thereof. In one variation, the one or more memory units can comprise an internal memory. In another variation, the one or more memory units can comprise an external storage unit. The one or more memory units can refer to a volatile memory or a non-volatile memory. For example, the one or more memory units can be a nonvolatile storage such as NVRAM, Flash memory, disk storage, or a volatile storage such as SRAM. The one or more memory units can be the main storage units for the device 100.

The system processor can be electrically coupled to the one or more memory units. The one or more memory units can store sleep-related programs created by a user of the device 100 using a client device 502 (see FIG. 5). The one or more memory units can also store music or sounds to be played by the main speaker 142 and/or the front speakers 128 of the device 100. The one or more memory units can comprise a non-volatile computer storage medium such as an electronically erasable programmable read-only memory (EEPROM). The one or more memory units can also comprise a flash memory and at least 16 MB of storage.

The system processor can also be electrically coupled to one or more amplifiers coupled to main speaker 142 and/or front speakers 128. The amplifiers can be used to adjust a volume of main speaker 142 and/or front speakers 128.

The system processor can be electrically coupled to a microphone for detecting sounds emanating from a room. For example, a user can run the application and listen to sounds coming from the room.

In some instances, the system processor can also be electrically coupled to a Bluetooth® audio interface to allow a user to transmit sounds or audio wirelessly from the client device 502 to be broadcast by the main speaker 142 and/or front speakers 128 of the device 100.

The system processor can also be coupled to the main LEDs 132 via a LED power control. The LED power control can be electrically coupled to the main LED board 134 or to part of PCB 156B.

Figure 5:
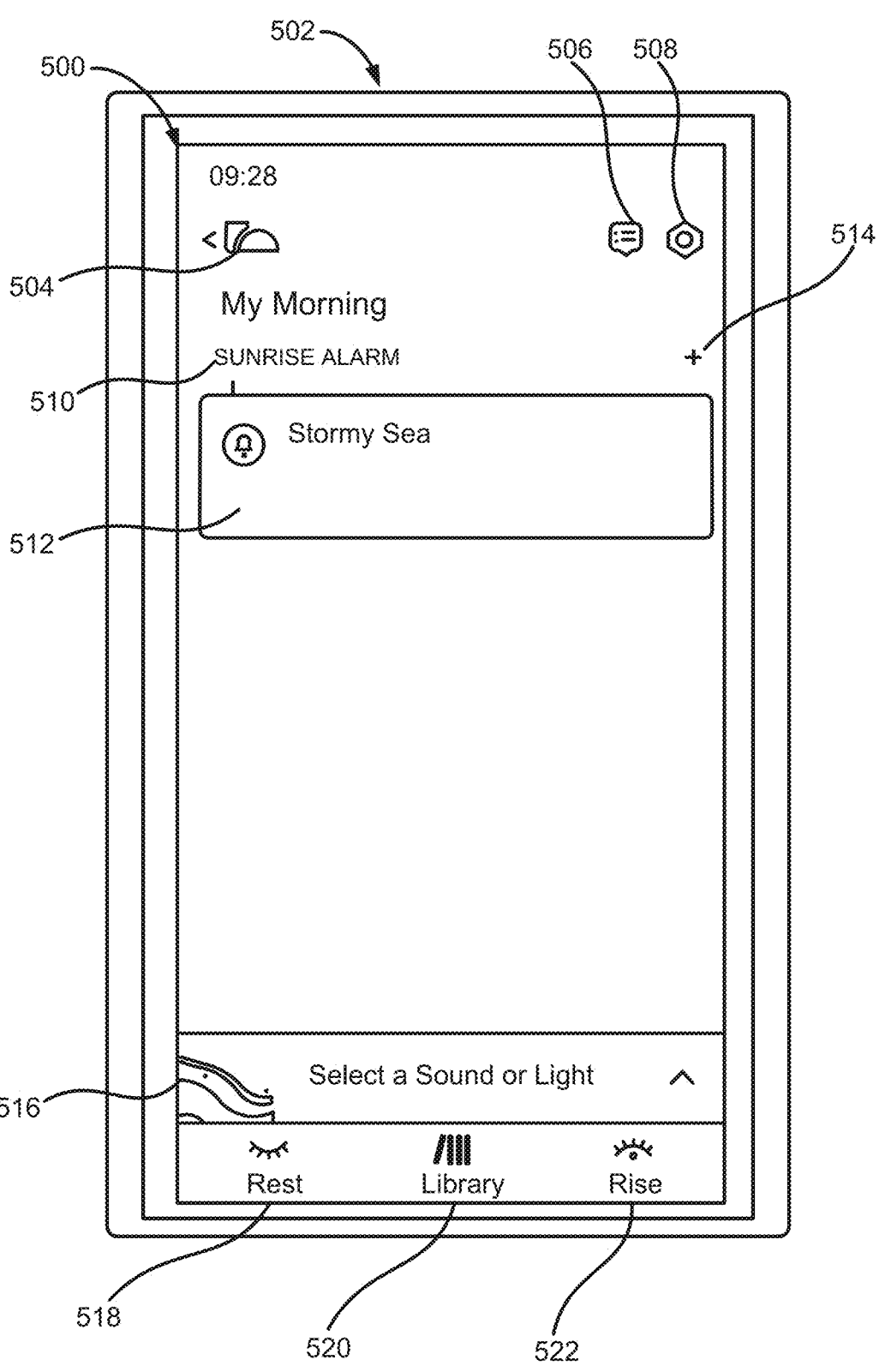
FIG. 5 illustrates an example graphical user interface (GUI) of an application running on a client device configured to allow a user to control the sleep training device.

FIG. 5 illustrates a client device 502 that can be used to control the sleep training device 100. The client device 502 can be in wireless communication directly with the device 100 through a short-range wireless communication protocol. The short-range wireless communication protocol can be a Bluetooth® protocol (such as a Bluetooth® Low Energy (BLE) protocol). The short-range wireless communication protocol can also be a ZigBee® protocol, a near-field communication (NFC) protocol, or any combination thereof.

The client device 502 can be a portable computing device such as a smartphone, a tablet, a laptop, a smartwatch, a personal entertainment device, a desktop computer, a workstation, another server, or a combination thereof. The client device 502 can have a client processor which can include one or more CPUs, GPUs, ASICs, FPGAs, or a combination thereof. The client processor can execute software stored in the client memory to execute the methods described herein. The client processor can be implemented in a number of different manners, for example, the client processor can be an embedded processor, a processor core, a microprocessor, a logic circuit, a hardware FSM, a DSP, or a combination thereof. As a more specific example, the client processor can be a 32-bit processor such as an ARM™ processor.

The client memory can store software, data, logs, or a combination thereof. In one variation, the client memory can be an internal memory. In another variation, the client memory can be an external storage unit. The client memory can be a volatile memory or a non-volatile memory. For example, the client memory can be a nonvolatile storage such as NVRAM, Flash memory, disk storage, or a volatile storage such as SRAM. The client memory can be the main storage unit for the client device.

The communication unit can be a wired or wireless communication interface. For example, the communication unit can be a network interface card of the client device. The communication unit can be a wireless modem or a wired modem. In one variation, the communication unit can be a WiFi modem. In other variations, the communication unit can be a 3G modem, a 4G modem, an LTE modem, a Bluetooth® component, a radio receiver, an antenna, or a combination thereof. The client device can connect to or communicatively couple with a WLAN, a wide area network, or a combination thereof using the communication unit. The client device can transmit or receive packets or messages using the communication unit.

The client device 502 can also have a display. The display can be a liquid crystal display (LCD) touchscreen, a lighting-emitting diode (LED) touchscreen, an active-matrix organic light-emitting diode (AMOLED) touchscreen, a super AMOLED touchscreen, or a combination thereof. In certain variations, the display can be a retina display, a haptic touchscreen, or a combination thereof. For example, when the client device is a smartphone, the display can be the touchscreen display of the smartphone.

Although not shown in the figures, it is contemplated by this disclosure that the client device 502 can be a standalone console or hub having a console processor, a console memory, a console communication unit, and a console display. The console or hub can be a dedicated wireless communication device for wirelessly connecting the device 100 with the client device 502.

The client device 502 can also be in wireless communication with the device 100 through a server and one or more networks. The networks can include any multi-hop network or wide area network (WAN) that covers regions, countries, continents, or a combination thereof. Examples of the networks can include a cellular network such as a 3G network, a 4G network or a long-term evolution (LTE) network, a satellite network; a sonic communication network; the Internet; or a combination thereof. The networks can include a number of wireless local area networks (WLANs). The WLANs can include networks established under the IEEE's 802.11 protocol or a successor thereof. For example, the WLANs can include a number of wireless-fidelity (WiFi) networks.

The server can have a processing unit, a memory unit, and a server communication unit. The processing unit can be coupled to the memory unit and the server communication unit through high-speed buses.

The sleep training device 100 and the client device 502 can also be part of a sleep training system.

Alternatively, the sleep training system can also comprise the sleep training device 100, the client device 502, and a voice-enabled assistance device. The voice-enabled assistance device can comprise an Amazon Echo™ device, an Amazon Echo Dot™, an Amazon Echo Spot™ device, an Amazon Echo Show™ device, a Google Home™ device, a Google Home Mini™ device, a Google Home Max™ device, or another smart home controller or hub device.

The sleep training device 100, the client device 502, and the voice-enabled assistance device can be communicatively coupled to a wireless local area network (WLAN) set up by a wireless gateway or wireless router. The sleep training device 100, the client device 502, and the voice-enabled assistance device can connect to another network (e.g., a WAN such as the Internet) via the wireless gateway or wireless router.

As previously mentioned, the client device 502 can also connect directly to the sleep training device 100 via a short-range wireless communication protocol (e.g., Bluetooth® or BLE).

The voice-enabled assistance device can communicate with a voice-enabled assistance server via the network. The voice-enabled assistance device can detect a voice command from a user to have the sleep training device undertake an action. For example, the action can include activating or deactivating the sleep training device; adjusting a volume level of sounds generated by the main speaker 142 and/or front speakers 128 of the sleep training device 100; playing, pausing, or resuming a track or sound stored in the memory of the sleep training device 100 or streamed by the sleep training device 100; initiating or stopping a timer function of the sleeping training device 100; adjusting a brightness or luminous intensity of light generated by the main LEDs 132; adjusting the color(s) of the light generated by the main LEDs 132; enabling or initiating a lock function, downloading multimedia content from the server or another device; downloading software updates from the server or another device; or a combination thereof.

The voice-enabled assistance device can parse the voice command and transmit the parsed voice command to the voice-enabled assistance server. The voice-enabled assistance server can process the parsed voice command based on stored rules and automation processes stored in one or more databases accessible to the voice-enabled assistance server. The voice-enabled assistance server can then transmit a corresponding instruction or command directly to the sleep training device 100 or to the server via one or more application programming interfaces (APIs) and the server can then transmit the instruction or command to the sleep training device 100.

The processing unit can include one or more CPUs, graphical processing units (GPUs), Application-Specific Integrated Circuits (ASICs), field-programmable gate arrays (FPGAs), or a combination thereof. The processing unit can execute software stored in the memory unit to execute the methods described herein. The processing unit can be implemented in a number of different manners. For example, the processing unit can be an embedded processor, a processor core, a microprocessor, a logic circuit, a hardware finite state machine (FSM), a digital signal processor (DSP), or a combination thereof. As a more specific example, the processing unit can be a 64-bit processor.

The memory unit can store software, data, logs, or a combination thereof. The memory unit can be an internal memory. Alternatively, the memory unit can be an external memory, such as a memory residing on a storage node, a cloud server, or a storage server. The memory unit can be a volatile memory or a non-volatile memory. For example, the memory unit can be a nonvolatile storage such as non-volatile random-access memory (NVRAM), Flash memory, disk storage, or a volatile storage such as static random-access memory (SRAM). The memory unit can be the main storage unit for the server.

The server communication unit can include one or more wired or wireless communication interfaces. For example, the server communication unit can be a network interface card of the server. The server communication unit can be a wireless modem or a wired modem. In one variation, the server communication unit can be a WiFi modem. In other variations, the server communication unit can be a 3G modem, a 4G modem, an LTE modem, a Bluetooth® component, a Bluetooth® Low Energy (BLE) component, a radio receiver, an antenna, or a combination thereof. The server can connect to or communicatively couple with a WLAN, a wide area network, or a combination thereof using the server communication unit. The server can transmit or receive data packets or messages using the server communication unit.

FIG. 5 illustrates an example graphical user interface of an application running on a client device 502 configured to control the sleep training device 100. Specifically, a rest GUI 500 can be rendered by the client device 502 to wirelessly and remotely control the device 100. The rest GUI 500 can be shown on a display of the client device 502 when a user opens or runs the application on the client device 502.

The rest GUI 500 can comprise a back button 504. The back button 504 can direct the user to a home page where they may access additional devices or add additional devices.

The rest GUI 500 can comprise a messages button 506. The messages button 506 can direct the user to a messages page where they may view various help messages, updates, or promotions regarding the device 100.

The rest GUI 500 can comprise a settings button 508. The settings button 508 can direct the user to options to view details regarding the device 100 such as firmware. The settings button 508 can also be used to direct the user to settings to auto-connect their client device 502 to the sleep training device 100 upon opening of the application.

The settings button 508 can also direct the user to view or change their personal account information. The settings button 508 can also provide links to help or support for the device 100.

The rest GUI 500 can comprise an alarm label 510, an alarm sound button 512, and an add alarm button 514. The alarm label 510 can indicate a name of the corresponding alarm (e.g., "SUNRISE ALARM"). There can be one or more alarms set at a time.

The alarm sound button 512 can comprise a name and image of the sound to be played upon activation of the alarm. The alarm sound button 512 can comprise a button to play the corresponding sound indefinitely such that the user can activate or deactivate the sound as desired. When the user presses the alarm sound button 512, the device 100 can emit sound via the main speaker 142 and the front speakers 128. The alarm sound button 512 can also direct the user to edit or delete the alarm.

The add alarm button 514 can direct the user to add and save an additional alarm. The user can choose the sound (or no sound), the light, the duration, and the volume of the alarm. The duration of the alarm can be set as a predetermined time period. Alternatively, or in addition, the alarm can be turned off by the user tapping the device 100. The user can also preview the alarm on the device 100 before saving the alarm as desired.

Figures 8, 9:
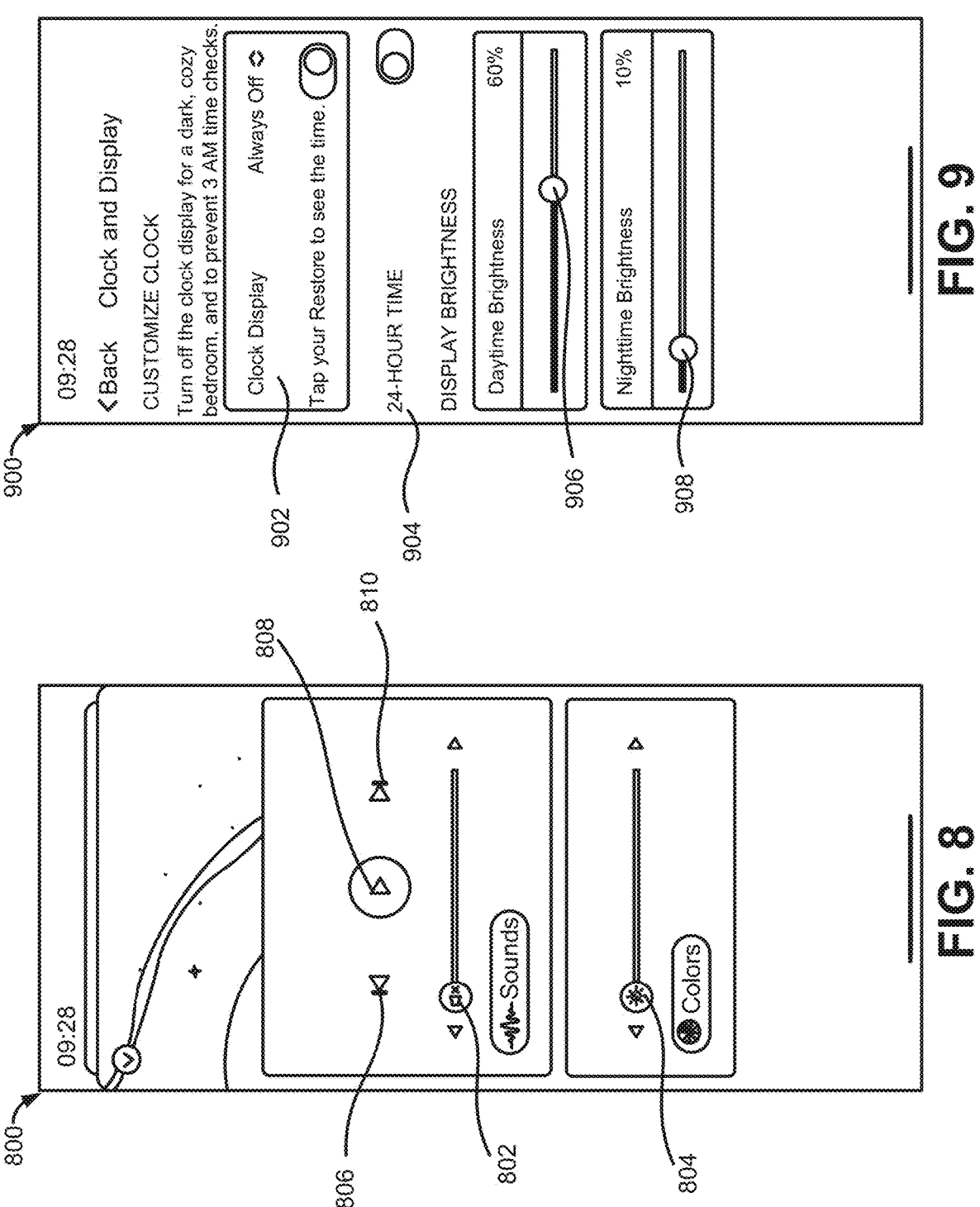
FIG. 8 illustrates a sound and light GUI of an application running on the client device configured to allow the user to control one or more sounds and/or colors of the sleep training device.
FIG. 9 illustrates a clock and display GUI of an application running on the client device configured to allow the user to control a clock display of the sleep training device.

The rest GUI 500 can comprise a sound and light menu 516. The sound and light menu 516 can direct the user to the sound and light GUI 800, as seen in FIG. 8 and as discussed further below.

Figure 6B:
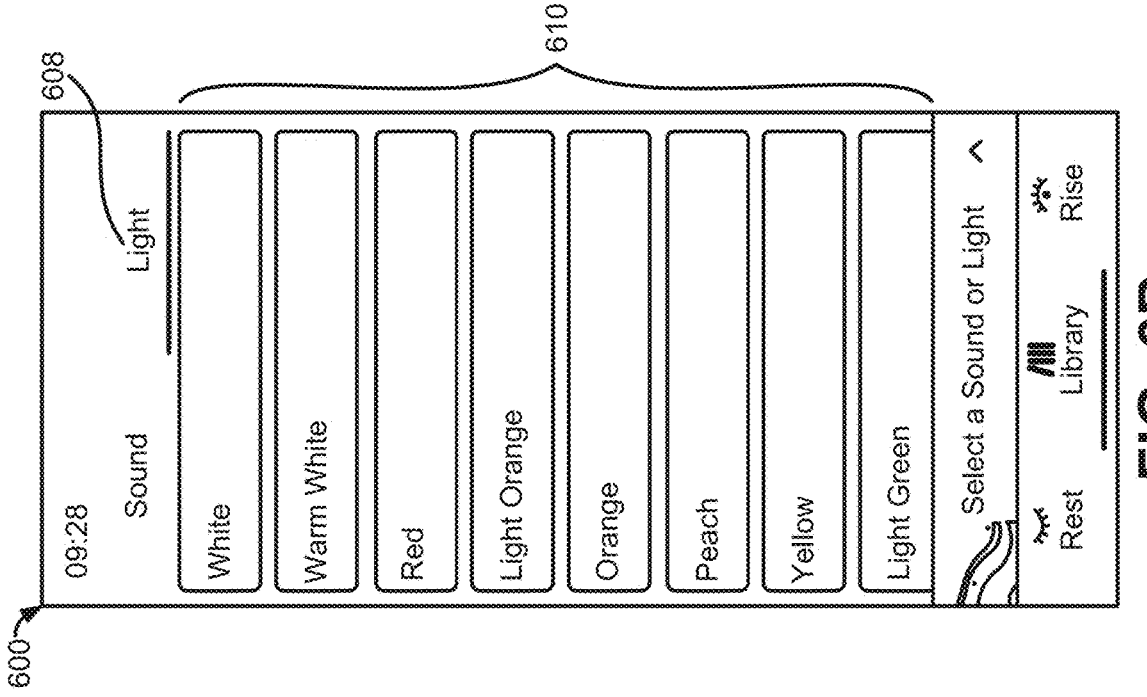
FIGS. 6A and 6B illustrate a library GUI of an application running on the client device configured to allow the user to set one or more alarm features of the sleep training device.
Figure 6A:
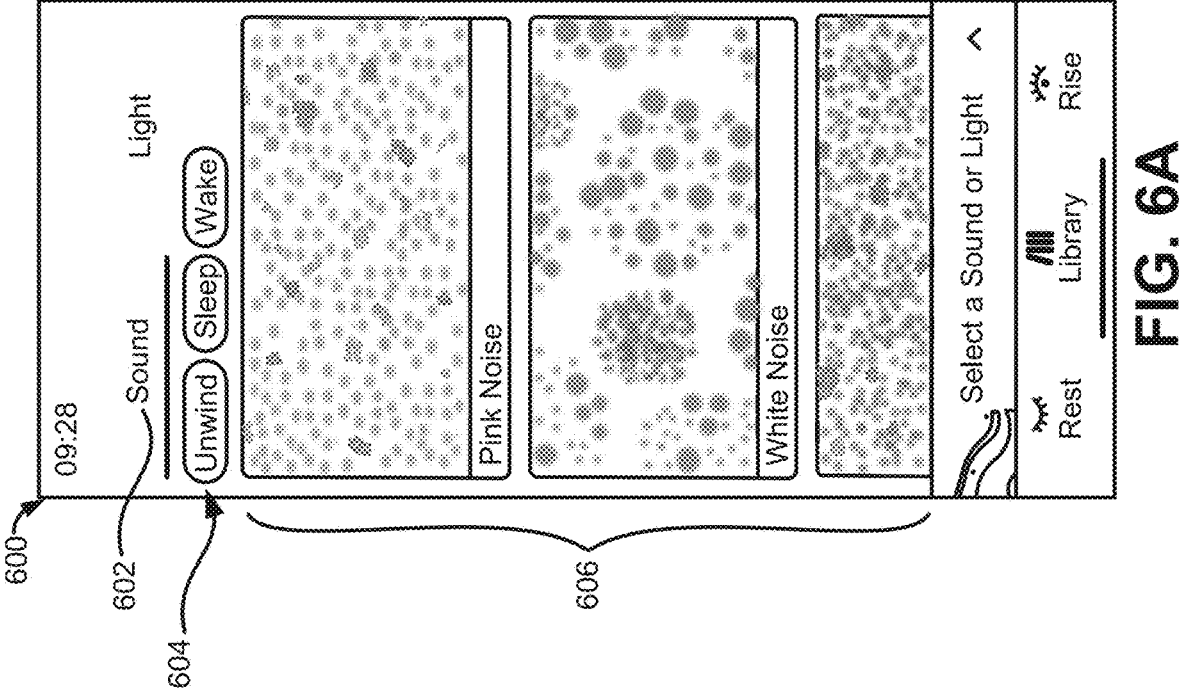
Figures 10A, 10B:
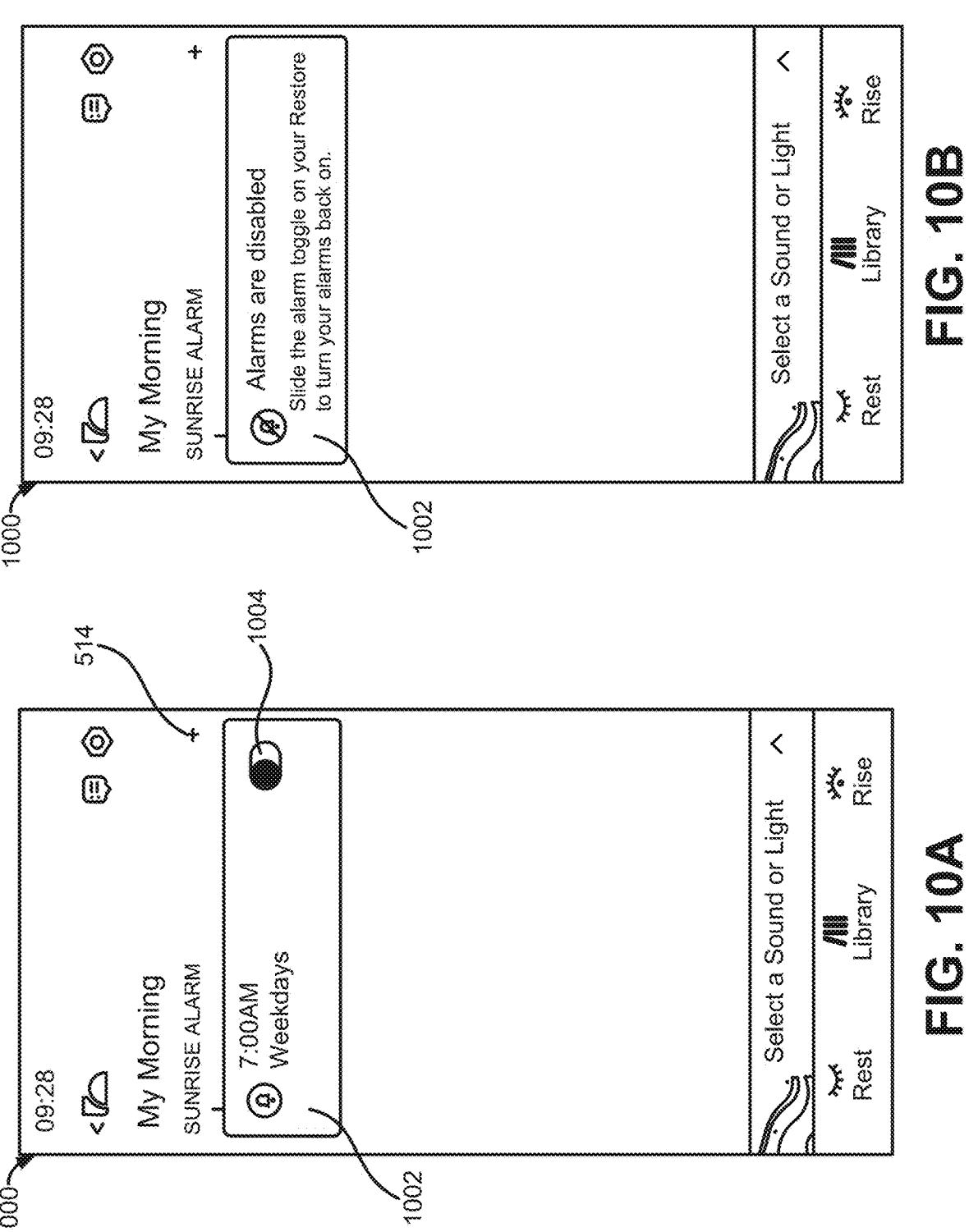
FIGS. 10A and 10B illustrate a rise GUI of an application running on the client device configured to allow the user to control one or more alarms set by the user.

The rest GUI 500 can comprise a GUI rest button 518, a GUI library button 520, and a GUI rise button 522. The GUI rest button 518 can direct the user to the rest GUI 500 as seen in FIG. 5. The GUI library button 520 can direct the user to the library GUI as seen in FIGS. 6A and 6B and as discussed further below. The GUI rise button can direct the user to the rise GUI 1000 as seen in FIGS. 10A and 10B and as discussed further below.

The rest GUI 500 and other GUIs can be rendered through an application written or coded using the Objective-C programming language, the Swift™ programming language, or a combination thereof. The application can also be written using the Java™ programming language, the Python™ programming language, the Objective-C programming language, or a C programming language.

FIGS. 6A and 6B illustrate a library GUI 600 of an application running on a client device 502 configured to set the alarm features of the sleep training device 100. The library GUI 600 can be displayed after the user provides input to the GUI library button 520.

As seen in FIG. 6A, the library GUI 600 can comprise a sound tab 602. The sound tab 602 can allow the user to select sounds applicable to a certain status of the device 100.

The user can choose from the status options 604: unwind, sleep, and wake. The unwind option can feature sounds that can provide the user to prepare for sleep with relaxing sounds, sleep stories, guided rest programs, or a combination thereof. The sleep option can comprise soothing sounds that can help the user sleep through the night. The wake option can provide affirmations, breathing exercises, and relaxing sounds or a combination thereof as the user wakes up.

The user can also choose from a library of sound options 606 desired for the corresponding status of the device 100. The sound options 606 can include a nature sound, a falling rain sound, a static white-noise sound, a bird chirp sound, a wind-blowing sound, an ocean wave sound, a babbling brook sound, a laundry machine sound, one or more pre-recorded tunes (e.g., a pre-recorded lullaby), or a combination thereof. The sound options 606 can be displayed or presented to a user through a number of sound selection buttons. Each of the sound selection buttons can have a graphic specially designed to associate a particular sound option 606 with the particular sound selection button.

The sound tab 602 can also present or display a mute button configured to instruct the device 100 to stop generating any type of sounds.

The application can provide a download option to download additional sounds or tunes to supplement or update the currently stored sounds or tunes. The additional sounds or tunes can be downloaded via WiFi (that is, received over WiFi from the server) or directly from the client device 502 via Bluetooth®. The additional sounds or tunes can be stored in the memory, on a memory card (e.g., a Secure Digital (SD) card) within the memory card slot, or a combination thereof. The additional sounds or tunes can also be downloaded into the memory from a memory card inserted into the memory card slot. The sound tab 602 can also be updated such that each new sound or tune has an associated sound selection button. The application can also provide a streaming option to stream new sounds via WiFi.

As seen in FIG. 6B, the library GUI 600 can comprise a light tab 608. The light tab 608 can allow the user to select lights emitted from the main LEDs 132 of the device 100. The user can choose from several color options 610 to instantly change the lights emitted by the main LEDs 132. Alternatively, the light of the device 100 can be programmed to display certain colors and/or brightness at desired times during the day.

The light tab 608 can present the user with a variety of color options 610 for changing the colors of the lights generated by the main LEDs 132. For example, the light tab 608 can give the user an option of selecting a substantially white light, red light, orange light, yellow light, green light, baby blue light, dark blue light, purple light, pink light, or a combination thereof.

Figures 7A, 7B:
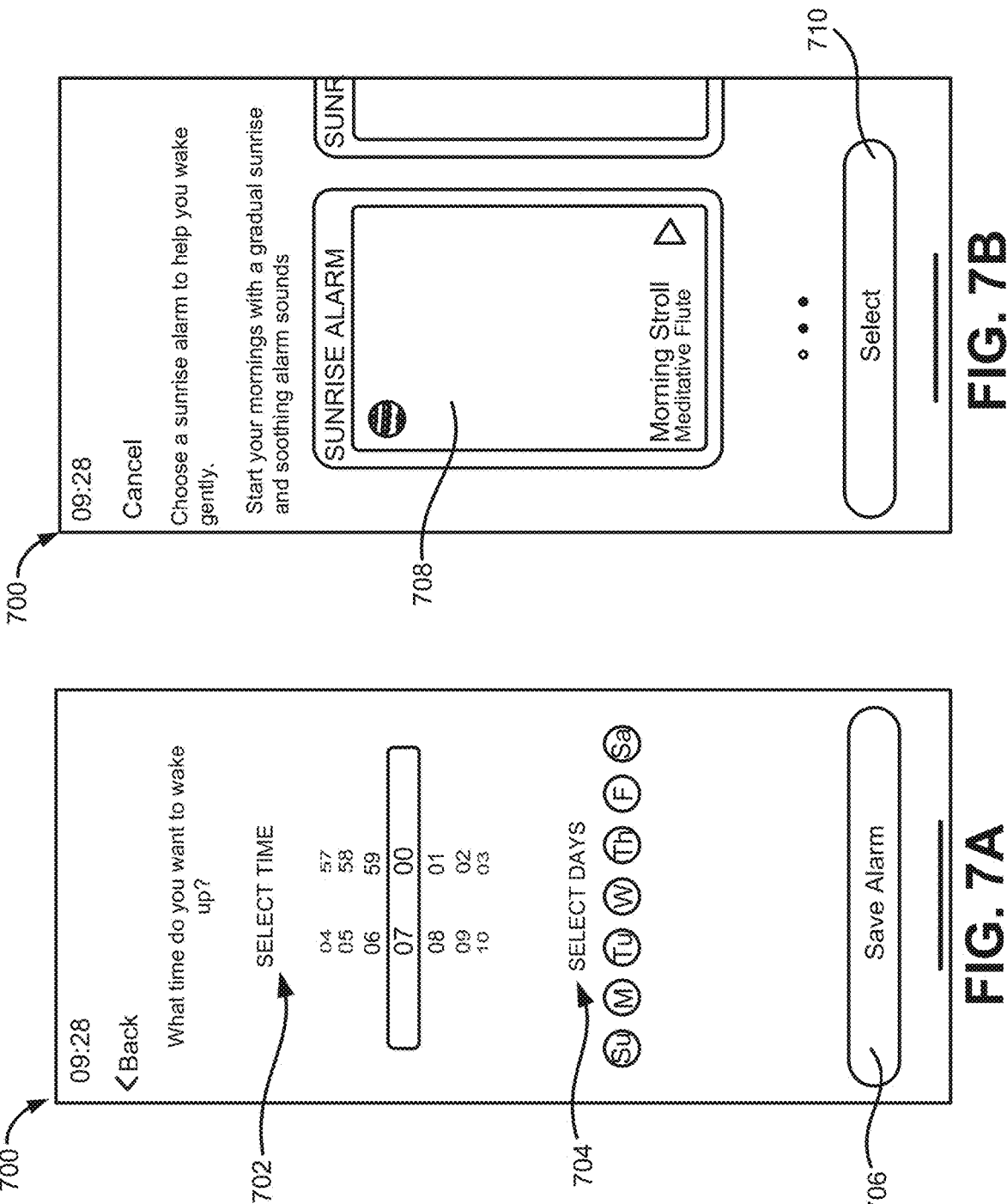
FIGS. 7A and 7B illustrate an alarm GUI of an application running on the client device configured to allow the user to control one or more alarms of the sleep training device.

FIGS. 7A and 7B illustrate an alarm GUI 700 of an application running on the client device 502 configured to control the alarm of the sleep training device 100. FIG. 7A illustrates that the application can render an alarm GUI 700 to set the alarm of the device 100. The alarm GUI 700 can present the user with a time menu 702 and a days menu 704. The user can select the desired time for a specific alarm via the time menu 702. The user can select the desired days for a specific alarm via the days menu 704. The user can repeat these functions for multiple alarms.

After a user selects a desired amount of time by saving the alarm via the save alarm button 706, the alarm GUI 700 can display the alarm sounds options menu 708. The user can choose from multiple sound options that can play from the device 100 at the selected time and date of the alarm. Once satisfied, the user can choose the desired sound via the select button 710.

Alternatively, the alarm GUI 700 can allow a user to set or schedule one or more sleep-related program. The sleep-related program can dictate when and for how long the device 100 automatically generates one or more lights or sounds. The sleep-related program can be scheduled based on a number of set parameters including a program start time, a program end time or duration, a program frequency or start dates, or a combination thereof.

The application can display a number of sleep-related program simultaneously. Each of the sleep-related program can be saved or stored in a client memory of the client device 502, a memory unit of the device 100, in one or more databases accessible to the one or more servers, or a combination thereof. A user can schedule or enable any of the previously stored or saved sleep-related program using toggle buttons displayed on the rest GUI 500. The client device 502 can transmit or send the sleep-related program set by the user to the device 100 via the server through WiFi, via a short-range wireless communication protocol, or a combination thereof. The sleep-related program can be stored in the memory of the device 100 when received by the device 100. The device 100 can initiate a sleep-related program when one or more set parameters (e.g., a program start time, a start date, etc.) associated with the sleep-related program are met.

The application can also display or render the alarm GUI 700 when a user applies an input to the add alarm button 514.

FIG. 8 illustrates a sound and light GUI 800 of an application running on a client device 502 configured to control the sounds and colors of the sleep training device 100. The sound and light GUI 800 can be displayed when the user provides input to the sound and light menu 516.

The sound and light GUI 800 can provide a volume control slider 802 and a brightness control slider 804. The volume control slider 802 can be used to remotely control the volume level of sounds generated by the main speaker 142 and the front speakers 128. The processor can instruct the amplifier to adjust the volume level of sounds produced by the main speaker 142 and the front speakers 128 in response to the user input applied to the volume control slider 802. The volume level of sounds generated by the main speaker 142 and the front speakers 128 can also be controlled by a user manually pressing one or more volume control switches 208 on the device 100.

The sound and light GUI 800 can also be used to adjust the volume of the sound as well as turn the sound off as desired. Accordingly, the device 100 can be used or function as a remote-controlled nightlight when a user places the device 100 in a room and runs the application on the client device 502 in order to select a lighting color from another room.

As described above, a user can also manually turn on the main LEDs 132 by touching the top of the outer housing 102 and adjusting the brightness of the main LEDs 132 by touching the one or more brightness control switches 206 on the front of the device 100.

The brightness control slider 804 can be used to remotely control a brightness or luminous intensity of the light generated by the main LEDs 132. The processor can instruct an LED power control to adjust the brightness or luminous intensity of the light in response to a user input applied to the brightness control slider 804.

As described above, a user can also manually control the brightness of the device by touching one or more brightness control switches 206 on the front of the device 100.

The sound and light GUI can also comprise a backward button 806, a play button 808, and a forward button 810. These buttons can be used to cycle through sounds playing from the device 100. The user can remotely cycle or reset a sound via backward button 806. The user can stop or play a sound via play button 808. The user can skip to a subsequent sound set in a sleep-related program via forward button 810.

FIG. 9 illustrates a clock and display GUI 900 of an application running on a client device 502 configured to control the clock display 204 of the sleep training device 100. The clock and display GUI 900 can be accessible via the settings button 508.

The clock and display GUI 900 can comprise a clock display feature 902. The clock display feature 902 can allow the user to turn the time display of the device 100 on or off. The clock display feature 902 can also allow the user to enable the user to tap the device 100 to activate the capacitive touch component 120 to temporarily display the time. The time can be displayed for about five seconds to fifteen seconds.

Alternatively, a 24-hour time feature 904 can be provided such that the time on the device can be displayed indefinitely upon activation.

The clock and display GUI 900 can comprise daytime brightness control slider 906 and nighttime brightness control slider 908. Daytime brightness control slider 906 can allow the user to control how bright the display of the clock is during the daytime. Nighttime brightness control slider 908 can allow the user to control how bright the display of the clock is during the nighttime. The brightness control sliders 906, 908 can also feature a percentage number to give a numerical indicator to the user regarding how bright the setting is.

FIGS. 10A and 10B illustrate a rise GUI 1000 of an application running on a client device 502 configured to control the set alarms of the sleep training device 100. The rise GUI 1000 can be displayed after the user provides a user input to the GUI rise button 522.

The rise GUI 1000 can display an alarm status 1002 for the one or more alarms set by the user. The alarm status 1002 can show the time and the days that the alarm has been set to alert the user via lights and/or sounds. The alarm can be disabled by the user via input on a slider 1004 on the rise GUI 1000. Alternatively, or in combination, the physical toggle switch 152 on the device 100 can be activated to disable the alarm. Additional alarms can be added via the add alarm button 514.

The sleep-related program can comprise one or more wind-down programs and wake-up programs. The wind-down programs can comprise instructions for the device 100 to generate light of a certain color from the LEDs for a specific period of time with or without sound. The wind-down programs can comprise instructions for the device 100 to generate or emit sound with or without lights. The wind-down program can be activated by pressing the rest button 148.

The user can select different stages of the wind-down program via the various GUIs above. The rest button 148 can be pressed again to transition the device 100 to the next stages of the wind-down program. The user can also hold rest button 148 to stop the wind-down program.

The wind-down program can comprise sounds and lights that remind a user of nighttime. Examples of lights can include custom configurations of lights that are dimmed to the user's desires. Examples of sounds can include white or pink noise, rain, wind, ocean sounds, fan sounds.

The wake-up program can include one or more instructions for device 100 to generate light of a certain color from the LEDs for a specific period of time with or without sound. The wake-up program can comprise instructions for the device 100 to generate or emit sound with or without lights. The wake-up program can be activated by pressing the rise button 150.

The user can select different stages of the wake-up program via the various GUIs above. The rise button 150 can be pressed again to transition the device 100 to the next stages of the wake-up program. The user can also hold rise button 150 to stop the wake-up program.

The wake-up program can comprise sounds and lights that remind a user of the morning. Examples of lights can include custom configurations of lights akin to sunrises, lighthouses, and dawn lights. Examples of sounds can include flutes, morning birds, or bells and alarms.

In addition to the wind-down program and the wake-up program, a user can set or schedule a naptime program, a bedtime program, an audio alarm program, a visual alarm program, or a combination thereof.

One technical problem faced by the applicant is how to design a sleep-related program to allow a user options for customizing both wind-down and wake-up routines. One technical solution discovered and developed by the applicant is to develop, in combination with the previously discussed physical features of the device, an application that allows a user to easily customize several stages of their routine. Therefore, a user does not have to worry about configuring a complicated GUI when setting an alarm. For example, the user can conveniently tap the rest button 148 or the rise button 150 after setting such sleep-related programs have been previously set via the client device 502. The sleep-related programs can promote good health by training the user to maintain a regular sleep routine that improves the user's general well-being.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps or operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit, or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to +0.1%, +1%, +5%, or +10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

It will be understood by one of ordinary skill in the art that the various methods disclosed herein may be embodied in a non-transitory readable medium, machine-readable medium, and/or a machine accessible medium comprising instructions compatible, readable, and/or executable by a processor or server processor of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A sleep training device, comprising:
an outer housing and a housing base, wherein the outer housing comprises a front side, a rear side, and a curved top;
a front panel at the front side of the outer housing;
a rear cover at the rear side of the outer housing;

a main speaker configured to produce sound, wherein the main speaker faces the rear side of the outer housing;
an internal reflector, wherein the front panel is coupled to an edge of the internal reflector;
a main speaker housing coupled to the outer housing, wherein the main speaker is coupled to the main speaker housing, wherein the main speaker housing is substantially shaped as a partial spherical segment,
wherein the main speaker housing, the internal reflector, and the main speaker create a sealed sound environment to control the sound produced by the main speaker; and
a front textile wrapped partially around the front panel, wherein the front textile comprises a woven fabric comprising warp threads running vertically and weft threads running horizontally, wherein a portion of the threads are undyed and wherein a portion of the threads are dyed.

2. The device of claim 1, wherein the main speaker housing is coupled to the internal reflector and is positioned rearward of the internal reflector, and wherein the main speaker faces a rear side of the outer housing.

3. The device of claim 1, further comprising a light dimming film positioned in front of a plurality of clock LEDs, and wherein the light dimming film is configured to dim light emitted by the plurality of clock LEDs.

4. The device of claim 1, further comprising a screen-printed layer covering a front face and edges of the front panel, and wherein the screen-printed layer is set via ultraviolet light.

5. The device of claim 1, further comprising a main LED dimmer positioned vertically over a plurality of LEDs, and wherein the plurality of LEDs face vertically upward.

6. The device of claim 1, further comprising a rear cover and a rear textile wrapped partially around the rear cover, wherein the rear textile comprises a woven fabric comprising warp threads running vertically and weft threads running horizontally, wherein the warp threads are undyed, and wherein the weft threads are dyed.

7. The device of claim 1, further comprising a capacitive touch component, wherein the capacitive touch component is configured to be activated via touch through a front textile.

8. The device of claim 1, wherein the outer housing is substantially shaped as a partial spherical segment.

* * * * *